(12) United States Patent
Lopez et al.

(10) Patent No.: US 8,114,464 B2
(45) Date of Patent: Feb. 14, 2012

(54) HYBRID THIN FILMS THAT INCORPORATE LAMELLAR PHOSPHOLIPID LAYER ASSEMBLIES AND TRANSMEMBRANE PROTEINS

(75) Inventors: Gabriel Lopez, Durham, NC (US); Plamen Atanasov, Sante Fe, NM (US); Gautam Gupta, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1200 days.

(21) Appl. No.: 11/690,922

(22) Filed: Mar. 26, 2007

(65) Prior Publication Data
US 2007/0269662 A1 Nov. 22, 2007

Related U.S. Application Data

(60) Provisional application No. 60/786,120, filed on Mar. 27, 2006, provisional application No. 60/785,699, filed on Mar. 24, 2006.

(51) Int. Cl.
*A61K 9/127* (2006.01)
(52) U.S. Cl. ........ 427/2.1; 427/2.24; 427/450; 427/484; 427/485; 427/486; 427/487; 427/488; 264/4.1; 264/4.3
(58) Field of Classification Search .......... 427/2.1–2.31; 424/450, 484–488; 264/4.1–4.3
See application file for complete search history.

(56) References Cited

U.S. PATENT DOCUMENTS

| | | | | |
|---|---|---|---|---|
| 5,989,587 A | * | 11/1999 | Sprott et al. | 424/450 |
| 6,048,546 A | * | 4/2000 | Sasaki et al. | 424/450 |
| 2002/0192843 A1 | * | 12/2002 | Kaganove et al. | 436/531 |

OTHER PUBLICATIONS

Buranda et al. Biomimetic Moleuclar Assemblies of Glass and Mesoporous Silica Microbeads for Biotechnology. Lagmuir 19, 2003, pp. 1654-1663.*
Baksh et al. Detection of molecular interactions at membrane surfaces through colloid phase transitions. Letters of Nature. 2004. pp. 139-141.*
Wagner et al. Tehered Polymer-Supported Planar Lipid Bilayers for Reconstitution of Integral Membrane Proteins. Biophysical Journal vol. 79 Sep. 2000pp. 1400-1414.*
Seddon et al. Chiral templating of Silica-lipid lamellar Mesophase with Helical tubular architecture. Angew Chem Int Ed Engl. Aug. 16, 2002;41(16) pp. 2988-2991.*

* cited by examiner

*Primary Examiner* — Timothy Meeks
*Assistant Examiner* — Cachet Sellman
(74) *Attorney, Agent, or Firm* — Gonzales Patent Services; Ellen M. Gonzales

(57) ABSTRACT

The present disclosure provides various novel methods for forming hybrid thin films that contain multi-lamellar assemblies of phospholipid bilayers and can incorporate proteins, polypeptides, biological complexes, transmembrane proteins and other membrane-associated compounds. The present disclosure further provides uses for such bilayer lipid membranes including, biosensing for medical diagnosis and environmental monitoring, chemical and biological warfare agent sequestration, actuator development, and bio-fuel cell development.

16 Claims, 10 Drawing Sheets

HYBRID THIN FILMS THAT INCORPORATE LAMELLAR PHOSPHOLIPID LAYER ASSEMBLIES AND TRANSMEMBRANE PROTEINS

CROSS-REFERENCE TO RELATED APPLICATIONS

The following application claims benefit of U.S. Provisional Application Nos. 60/785,699, filed Mar. 24, 2006, and 60/786,120, filed Mar. 27, 2006, each of which is hereby incorporated by reference in its entirety.

STATEMENT REGARDING GOVERNMENT SPONSORED RESEARCH

Aspects of this work were supported by a grant from the Department of the Army through grant no. DAAD19-03-1-0173. The United States Government has certain rights in the subject matter.

TECHNICAL FIELD

The present invention relates to hybrid thin films. More specifically the present invention relates to methods for incorporating polypeptides, biological complexes, transmembrane proteins and other membrane-associated components into hybrid thin films and methods of using the same.

BACKGROUND

Phospholipids are a major component of all biological membranes. In its simplest form, a phospholipid is composed of glycerol bonded to two fatty acids and a phosphate group. Due to its polar nature, the head of a phospholipid is hydrophilic while the nonpolar tails are hydrophobic. When placed in water, phospholipids form a bilayer, composed of a hydrophobic core region formed by the acyl chains of the lipids, and hydrophilic membrane interfacial regions that are formed by the polar head groups of the lipids.

Membranes made of phospholipid bilayers are partially permeable, very flexible, and have fluid properties in which embedded proteins and phospholipid molecules are constantly moving laterally across the membrane. Proteins incorporated into the phospholipid bilayer can facilitate actions such as compartmentalization, passive and active transport, signal transduction, specific recognition, and energy utilization.

Because of their versatility in function, scientists have long sought to incorporate phospholipid bilayer membranes into artificial materials and devices. These devices have a broad range of potential applications including ligand based biosensors for clinical diagnostics; memory devices; screening devices for pharmaceutical applications; the provision of biologically functionalized surfaces; binding sites for small molecules such as drugs, pesticides, molecules required to be analyzed during process control (i.e. food stuffs, fermenter products, chemicals); larger molecules such as proteins for research screening (e.g. array technology) or diagnostics (cancer markers, infectious disease markers, hormones); nucleic acids; carbohydrate polymers; cells such as pathogenic bacteria; eukaryotic cells such a cancer cells and small single or multicellular organisms especially parasites; high throughput screening for pharmaceutical applications; controlled drug delivery; medical diagnosis; environmental monitoring, chemical and biological warfare agent sequestration; actuator development; power sources; electrochemical pumps; and bio-fuel cell development.

However, phospholipid bilayer membranes are inherently fragile. Due to their thinness, polar charge, tendency to naturally curve, and the inherently weak self-assembly forces at work, they are subject to disruption from phenomenon such as vibration, sonication, chemical reaction, pH, temperature denaturing, electromagnetic fields and the like making them unsuitable for applications outside of the most stringently controlled conditions. Additionally, it has been difficult to create membranes with uniform nanostructures capable of incorporating other proteins such as transmembrane proteins in nonrandom orientations.

There is therefore a need for the creation of stable membranes capable of mimicking natural biological processes. There is additionally a need for the creation of stable membranes which contain uniform nanostructures amenable to the incorporation of biomolecular complexes in nonrandom orientations.

SUMMARY OF EXEMPLARY EMBODIMENTS OF THE INVENTION

The present disclosure provides various novel methods for forming hybrid thin films that contain multi-lamellar assemblies of phospholipid bilayers and can incorporate proteins, polypeptides, biological complexes, transmembrane proteins and other membrane-associated compounds. The present disclosure further provides uses for such bilayer lipid membranes including, biosensing for medical diagnosis and environmental monitoring, chemical and biological warfare agent sequestration, actuator development, and bio-fuel cell development.

DETAILED DESCRIPTION

Figure 1A:
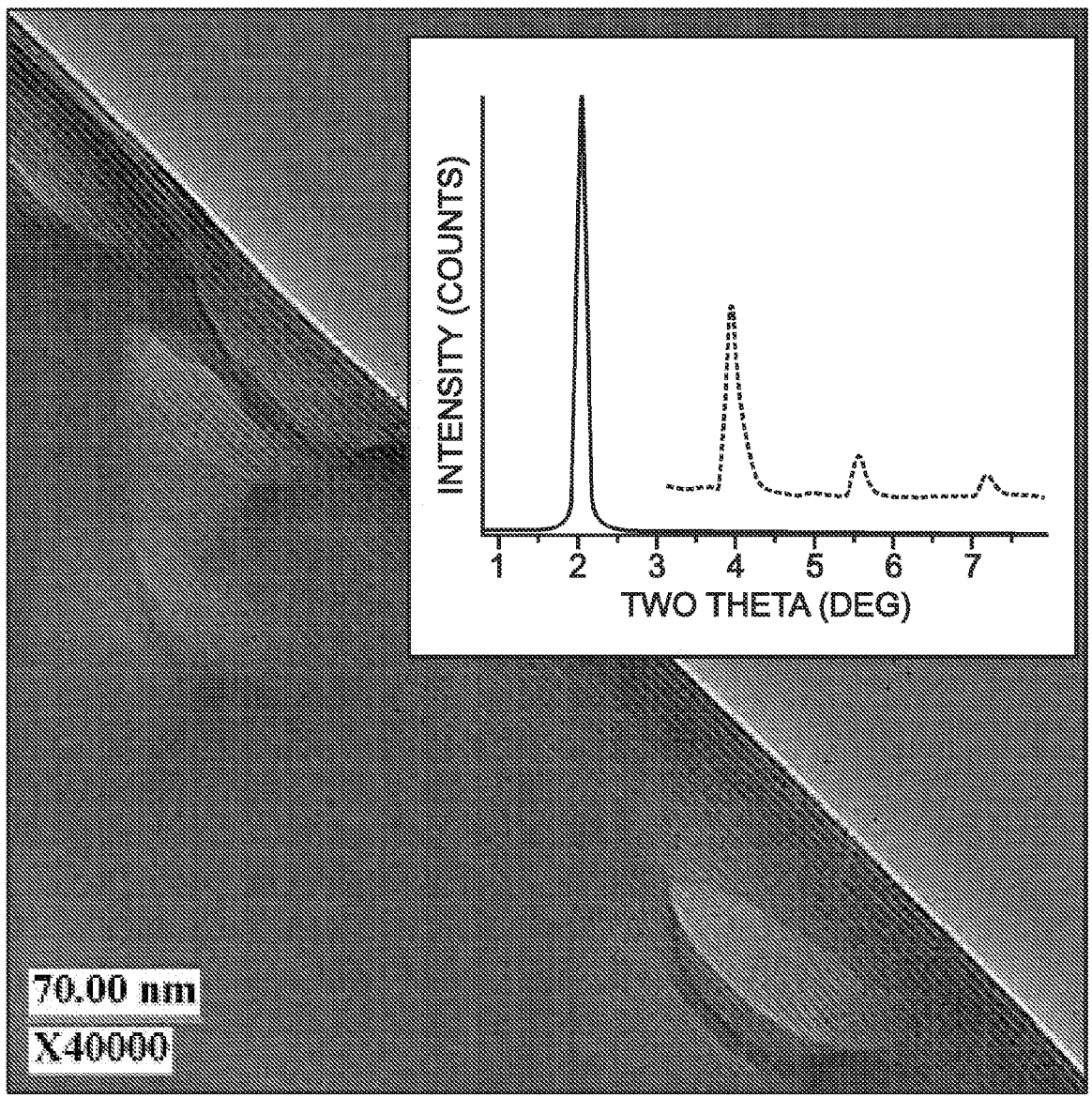
FIGS. 1A and B show TEM micrographs of the surface and the x-ray diffraction pattern (inset) of a lipid-silica thin film (2.5 wt % lipid in stock sol) made with (A) 1,2-dimyristoyl-sn-glycero-3-phosphocholine (DMPC) and (B) 1,2-dioleoyl-sn-glycero-3-phosphocholine (DOPC).

The present invention provides methods for preparing hybrid bioorganic-inorganic thin films with specific architecture. Such thin films can be used in a variety of applications including, but not limited to, biosensors, medical diagnosis, environmental monitoring, chemical and biological warfare agent sequestration, actuator development, power sources, sensing platforms, electrochemical pumps, and bio-fuel cell development.

The present invention further provides methods for preparing hybrid bioorganic-inorganic thin films that can exhibit selective and active transport function.

The present invention additionally provides methods for preparing functional biosynthetic cell membrane components encapsulated in nanostructured membrane architectures.

Phospholipid bilayer membranes are essential components of cellular systems. They enable a variety of functions including compartmentalization, passive and active transport, signal transduction, specific recognition and energy utilization. Formation of phospholipid bilayers is influenced by factors such as the surfactant used, pH, salt concentration, type of solvent and temperature at which the assemblies are synthesized.

The thin films formed by the methods herein are artificial assemblies which self assemble with phospholipids and phospholipid mixtures into micellar and lyotrophic liquid crystalline phases. For example, in some embodiments, a lamellar structure may be constructed in which hydrophilic crosslinked polymer nanophases are separated by parallel lipid bilayers. In additional embodiments, the lamellae are parallel to the film surface. In other embodiments, the lamellar assemblies are highly ordered. The thin films contain uniform nanostructures that are amenable to the incorporation of functional amphiphilic proteins, peptides and other biomolecular complexes in nonrandom orientations.

The nanostructures created by the methods of the present invention may be planar or vesicle like. In some embodiments, the structures exhibit uniform d-spacing of between 35 to 48 Å. In other embodiments the uniform d-spacing is 44 Å. In additional embodiments, the polymer and phospholipid bilayers may alternate. In further embodiments, processing conditions may be altered to effect the orientation of the transmembrane protein or other biomolecular complex.

The scale of these thin films may be from about 5 to about 500 nm, about 5 to about 100 nm or about 5 to about 50 nm in width. In another embodiment, liposomes may be formed using lipid-polymer hybrid membranes. These liposomes may be about 40 nm to about 100 nm, and more preferably about 50 to about 100 nm. Thin films incorporating phospholipid bilayer assemblies may be constructed using saturated or unsaturated lipids with a packing fraction parameter of between 0.5 to 1. In some embodiments, the thin films may contain highly ordered lyotrophic crystalline surfactant phases encapsulated in rigid silica matrices.

The thin films of the present invention are generally formed using a precursor sol, solvent, acid, water and dried phospholipids. The precursor sol may be formed by combining a polymer or hydrogel, a solvent, and water. Exemplary polymers for use within the methods and compositions of the present invention include, but are not limited to, inorganic polymers such as tetramethylorthosilicate, tetraethylorthosilicate, aminopropyltrimethyoxysilane, hydroxymethyltriethoxysilane, methacryloxypropyl trimethoxysilane, and hydroxyethyl methacrylate; organic polymers including nonionic organic polymers such as poly (vinyl alcohol), poly (vinyl pyrrolidone), poly (ethylene oxide), hydroxy-propyl cellulose, dextran, agarose, dissacharides: sucrose, glucose and trehalose; anionic organic polymers such as poly (acrylic acid), poly (sodium styrene sulphonate), poly acrylamide (PAM), alignate, chitosan-EDTA, carbomer, pectins, DNA; cationic organic polymers including, but not limited to, poly (diallyldimethylammonium chloride), chitosin, and polylysine or combinations thereof. The polymer precursors impart toughness and rigidity to the membranes while the hydrogel precursors provide a highly water swollen matrix that is believed to facilitate diffusion of water soluble analyte species. Exemplary solvents include alcohols such as, for example, ethanol, methanol, and isopropyl alcohol. Exemplary acids include HCl.

In some embodiments, the polymer may be silica based. Exemplary silicas include, but are not limited to, tetraalkoxysilanes such as tetraethylorthosilicate or tetramethyl-orthosilicate; trialkoxysilane such as aminopropyltrimethyoxysilane, hydroxymethyltriethoxysilane or methacryloxypropyl trimethoxysilane; or combinations thereof. Such polymers form a matrix, for example through a siloxane condensation reaction, whose nanostructure may be determined by the organized lipid structures.

Figure 10:
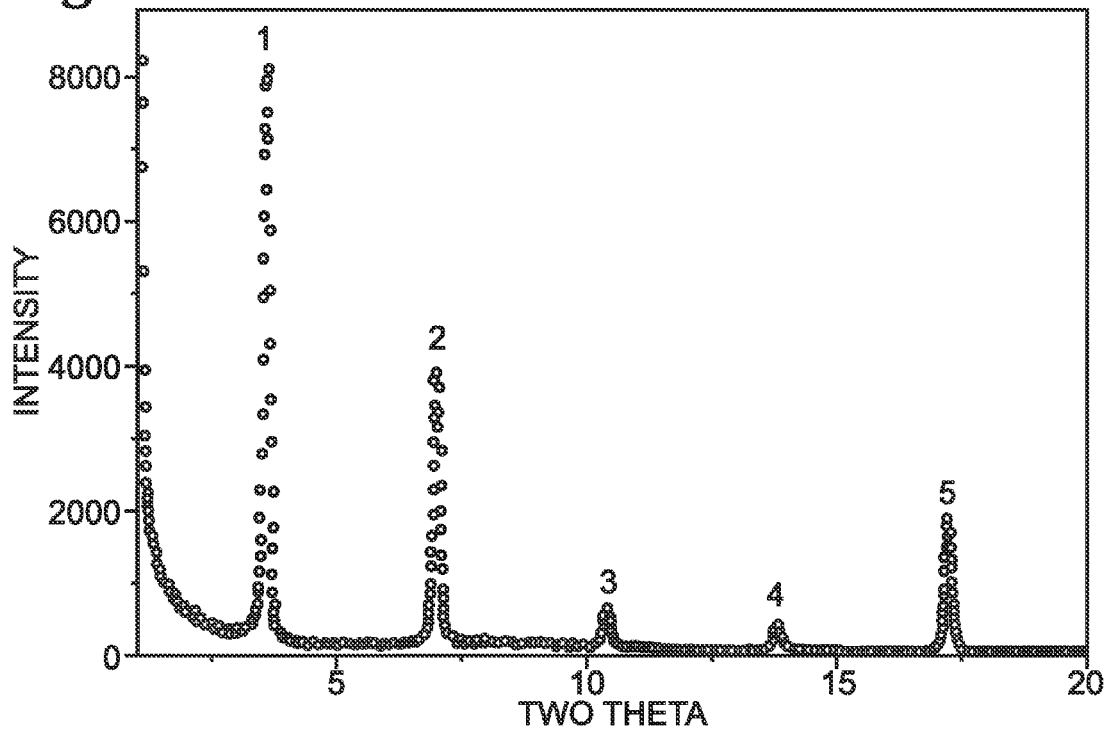
FIG. 10 is the x-ray diffraction pattern for lipid-silica matrices demonstrating that the positions of the diffraction peaks were in integer multiples indicating the lamellar nature of CTAB in the silica matrix.

In additional embodiments, surfactant may be added to the precursor sol. Any surfactant which forms a lamellar structure in the polymer matrix may be used. The lamellar nature of the surfactant may be determined by any means applicable. In one embodiment the structure of a film constructed using a surfactant may be determined through x-ray diffraction as seen in FIG. 10. FIG. 10 depicts the x-ray diffraction pattern for a highly ordered nanostructured silica/surfactant membrane prepared using cetyltrimethyl ammonium bromide (CTAB), aminopropyltrimethoyoxysilane and the exemplary phospholipids listed below. The positions of the diffraction peaks in FIG. 10 are in integer multiples indicating the lamellar nature of CTAB in the silica matrix.

Exemplary surfactants for use within the compositions and methods of the present invention include, but are not limited to, ionic surfactants such as cetyltrimethyl ammonium bromide (CTAB), and nonionic surfactants such as Pluronic-P 123 (poly(ethylene oxide E0)20(propylene oxide P0)70(E0) 20).

Lipids for use within the methods and compositions of the present invention may include saturated or unsaturated lipids. The selection of particular lipids and the concentration of lipids may depend in part on the type of resulting thin film and nanostructures to be obtained. In some embodiments, the lipids form 0.01-50% wt of the resulting solution. In other embodiments, the lipids from between about 1 to 30% wt, preferably about 5 to 20% wt, more preferably about 5 to 10% wt, more preferably 0.01 to about 10% weight of the resulting solution. The concentration of the lipids may effect the d spacing of the lamellar structures. In some embodiments, an increase in the concentration of the lipid may be used to increase the d spacing in the resulting nanostructures.

The selection of a particular lipid may be based on a number of factors including, but not limited to, the packing coefficient, charge, the length of the tails, and the number of chains per headgroup. Potential structures may be predicted by determining the packing parameters of the lipids used to construct the membranes. Different packing parameters or shape factor g ($v_{hc}/a_o l_c$) of amphiphiles, where $a_o$ is the optimal head group area, $l_c$ is the critical length of the hydrocarbon chain, and $v_{hc}$ is the volume of hydrocarbon chains, may be used to predict or interpret the microstructure of lipid-polymer assemblies. Different parameters may generate lamellar, hexagonal or cubic structures. For example, a lamellar phase, such as that created by the methods of the present invention, is obtained when the packing fraction parameter is between 0.5 to 1.

The packing parameter of DMPC is calculated to be 0.577 using the equations and values given below $$V_{hc} = 2 \cdot [(n_c - 2) \cdot v_{CH2} + v_{CH3}]$$

The head group area for a PC molecule is estimated to be 62 Å$^2$. $V_{hc}$ is the hydrocarbon chain volume of the two acyl chains with $v_{CH2}=27$ Å$^3$ and $v_{CH3}=54$ Å$^3$. The maximum extended chain length of the phospholipids is given by the relation $$l_c = 1.25(n-1) + 0.85 + d$$

where d is the displacement of the chains. (4 Å) (Kleinschmidt, J. H.; Tamm, L. K. *Biophysical Journal* 2002, 83 994-1003).

Using these values, the packing fraction parameter for the lipid DMPC is as follows:

$$g = v_{hc}/a_o l_c = 0.577$$

However, using the methods of the present invention, the head group area, $a_o$ is effectively increased by approximately 10% due to the positive charge on the DMPC molecule at pH 2.2, where the phosphate group is protonated. The net packing parameter of DMPC molecule with pH factor taken into account is therefore as follows:

$$g = v_{hc}/a_o l_c = 0.525$$

indicating the possibility of the formation of lamellar phase in DMPC-polymer assemblies.

Figure 1B:
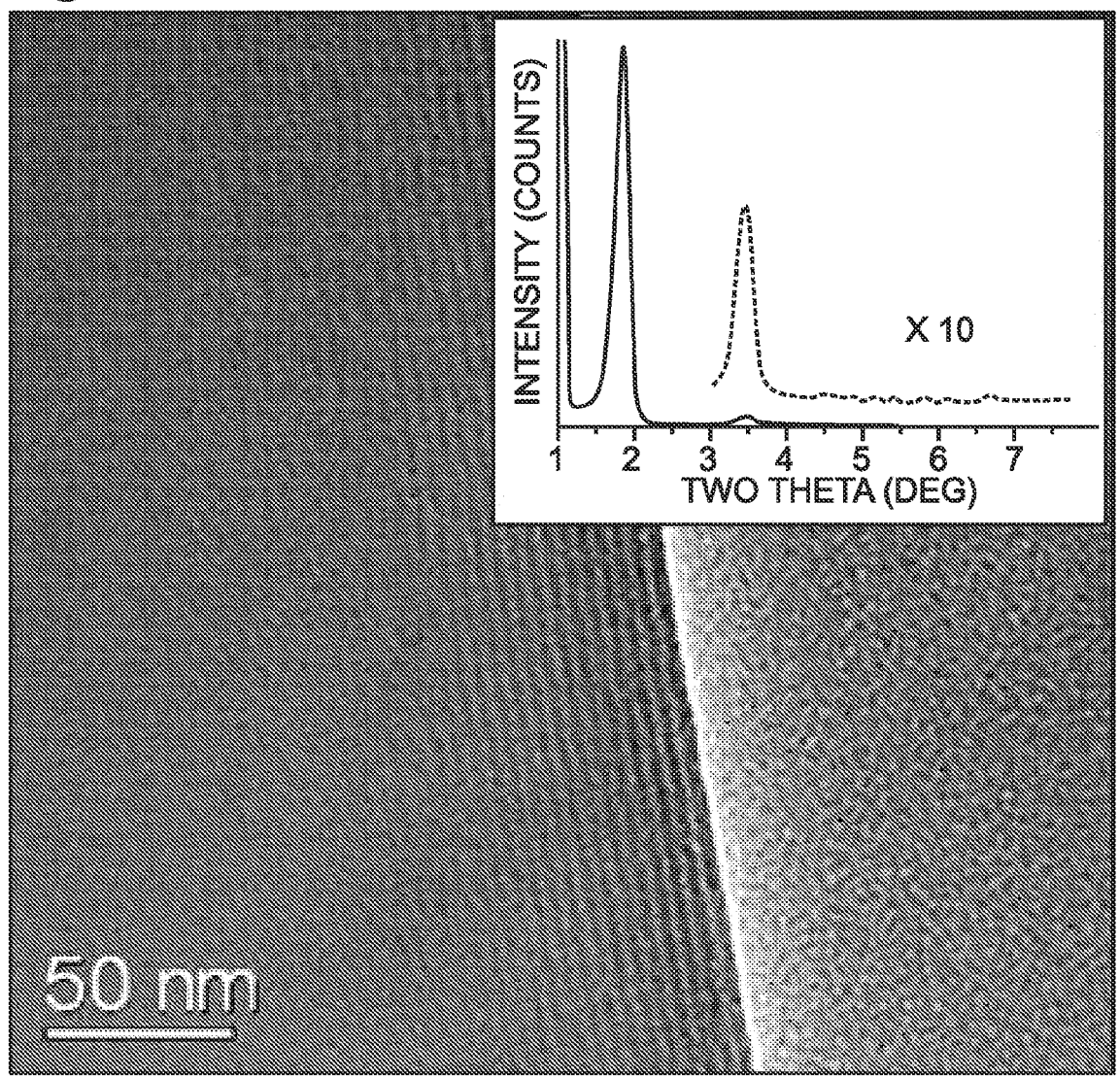

Packing parameters vary depending on whether saturated or unsaturated lipids are used. The contrast in the packing parameters of saturated and unsaturated lipids in the hybrid phospholipid-silica thin film assemblies of the present invention can be seen, for example, in a comparison of FIGS. 1A and 1B. In FIG. 1A, d spacing observed for film created using DMPC is 42 to 44 Å. Four order of diffraction peaks are observed for saturated lipids with a peak ratio is 1:2:3:4. In FIG. 1B, d spacing for a film created using DOPE is approximately 47 Å with a first order diffraction peak at 47 Å and a second order peak at 24 Å. These results indicate that the saturated lipids are better packed than unsaturated lipids.

The length of the lipid chain also influences the end structure of the thin film. As demonstrated in the examples below, lipids with chain lengths of 14 carbon atoms yield a d-spacing of 42-44 Å whereas lipids with a chain length of 18 carbon atoms yield a d-spacing of 47-49 Å. It was therefore determined that there was an increase in d-spacing of approximately 1.2 Å for each carbon added to the chain.

The structure of thin films may additionally be influenced by the number of chains per headgroup. Thin films were prepared as detailed in the examples below using MHPC, DMPC, and cardiolipin, three saturated lipids each with a chain length of 14 carbon atoms. MHPC is a single tailed lipid, DMPC has two chains and cariolipin has 4 chains. The d-spacing observed for the three lipids was 42 Å, 44 Å and 46 Å respectively. The difference in the spacing may be explained by the stiffness of the hydrocarbon tails with single chain lipids having more flexible tails.

Figure 4A:
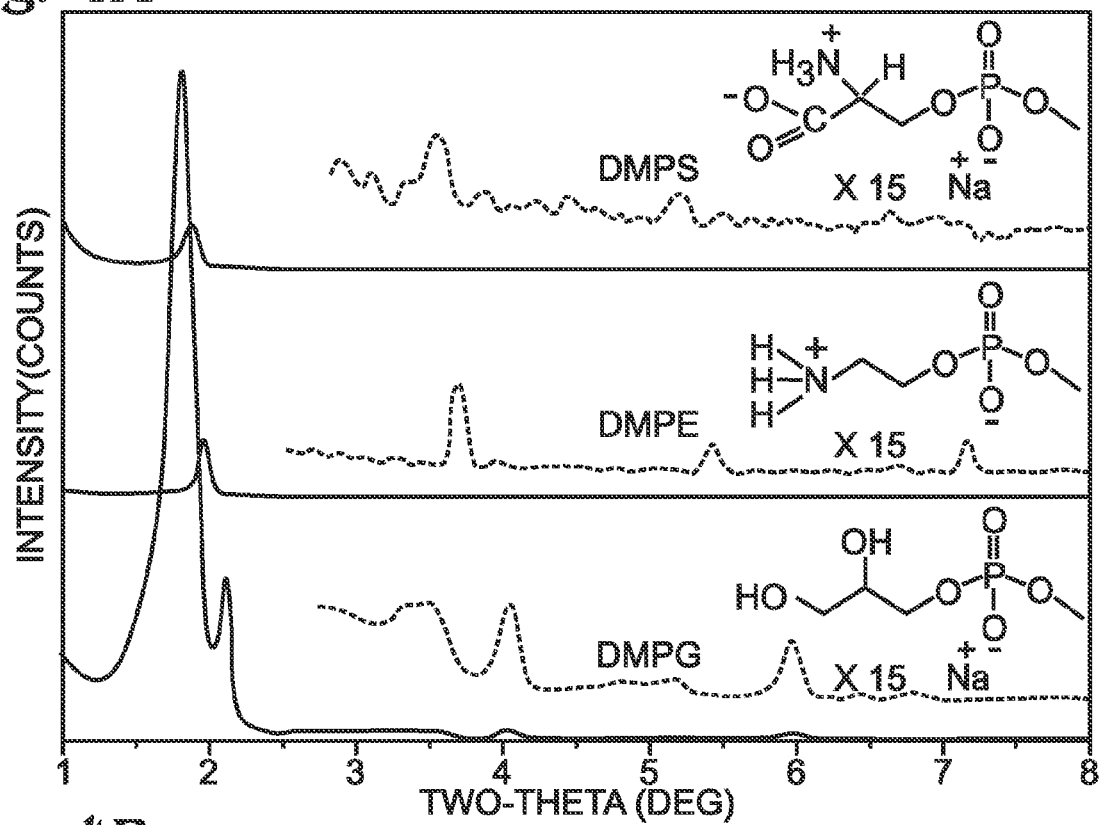
FIGS. 4 A and B are x-ray diffraction patterns of 2.5 wt % lipid-silica assemblies made using (A) saturated or (B) unsaturated lipids.
Figure 4B:
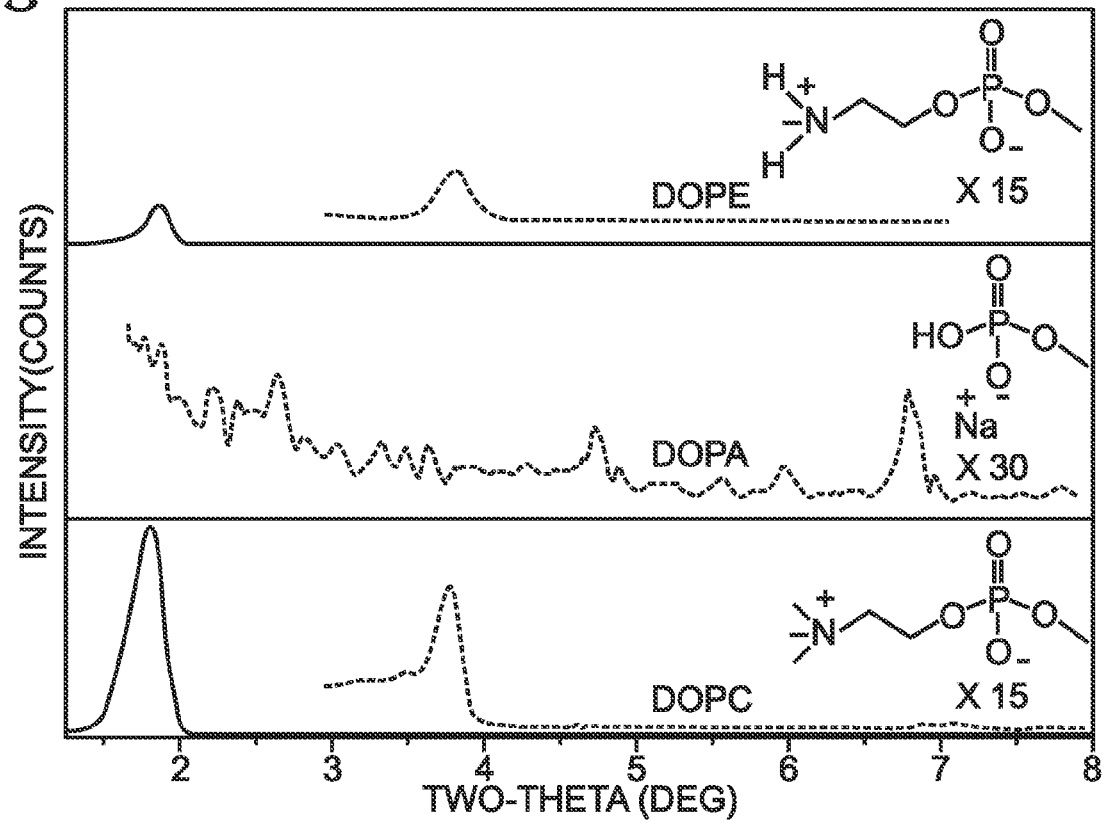

Additionally, as can be seen in FIG. 4, the charge of the headgroup effects membrane formation. Lipids with a positively charged headgroup at pH 2.2 and lipids capable of hydrogen bonding yield lamellar-lipid silica assemblies of the present invention, whereas lipids with neutral or negatively charged headgroups failed to form the desired structures. While not wishing to be bound, it is currently theorized that the charge may influence the effective size of the head group of the lipid, thereby altering the packing parameter and hence the formation of the lipid assembly.

Exemplary phospholipids for use within the invention include, but are not limited to, 1,2-dimyristoyl-sn-glycero-3-phosphocholine (DMPC; 14:O); 1,2-dimyristoyl-sn-glycero-3-phosphoethanolamine (DMPE; 14:O); 1,2-dimyristoyl-sn-glycero-3-[phospho-rac-(1-glycerol)] (Sodium Salt) (DMPG, 14:O); 1-myristoyl-2-hydroxy-sn-glycero-3-phosphocholine (14:O Lyso PC); 1,2-dioleoyl-sn-glycero-3-phosphocholine (DOPC; 18:1 (cis)); 1-oleoyl-2-hydroxy-sn-glycero-3-phosphoethanolamine (18:1 Lyso PE); 1,2-dioleoyl-sn-glycero-3-phosphoethanolamine (DOPE, 18:1); L-phosphatidylcholine (Egg, Soy); Phosphatidylcholine (NBD); 1,1',2,2'-tetramyristoyl cardiolipin (Ammonium Salt) (14:O); lipids with head groups phosphatidyl serine and phosphatidylinositol; poly(ethylene glycol)-lipid conjugates; and fluorescent lipids-phosphatidylcholine (NBD) or combinations thereof In some embodiments, cholesterol may be added to mixtures containing unsaturated lipids. Cholesterol may be added to the dried lipid, the precursor sol, or a combined mixture of dried lipid and precursor sol in varying concentrations from about 0 to 50% weight of the lipid mixture, preferably about 10 to 40% weight, more preferably about 15 to 30% weight.

The selected lipids are hydrated in the precursor sol to form a lipid-polymer solution. The resulting solution may be homogenized. Such a homogenized solution may be further treated, for example, through sonication or extrusion.

Such solutions, regardless of homogenization, may then be used to form the hybrid thin films of the present invention. In some embodiments, such thin films may further incorporate additional biomolecular complexes including transmembrane proteins which may be used in the transport of solutes. Such biomolecular complexes may be incorporated with specific orientations. The particular orientation of a biomolecular complex may be varied depending on the conditions used. Such variation may effect the flow of the analyte species transported by the biomolecular complex.

In previous artificial membranes, the transport rate of aqueous solutes, particularly larger ions and molecules was inhibited by dense crosslinking of polymers between the lipid bilayer structures. The degree of crosslinking in embodiments of the present invention may be reduced by changing the condensation conditions or through the incorporation of comonomers into the precursor sol that are not capable of quadravalent bonding. Exemplary comonomers as used in the present invention include, but are not limited to, aminopropl-trimethoxysilane, hydroxymethyltriethotysilane and methacryloxypropyl trimethoxysilane.

The resulting synthetic and hybrid biosynthetic membranes of the present invention have unprecedented levels of specificity towards aqueous solutes. In addition to selective ion channels and molecular channels, the membrane systems of the invention can include transmembrane proteins that are involved in active transport by proton, ion and molecular pumping mechanisms.

Biomolecular complexes may be included in the membranes by combining the lipids with additional proteins or peptides prior to hydration. In other embodiments, such biomolecular complexes may be included by adding them directly to the precursor sol either before or after the addition of lipids.

Exemplary biomolecular complexes including proteins and peptides that may be incorporated into the hybrid thin films of the present invention include, but are not limited to, g protein coupled receptors including, but not limited to, Class A (Rhodopsin-like) G protein coupled receptors which bind amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and LPA; G protein coupled receptors with amine ligands including, but not limited to, acetylcholine or muscarinic, adrenoceptors, dopamine, histamine, serotonin or octopamine receptors; peptide ligands including, but not limited to, angiotensin, bombesin, bradykinin, anaphylatoxin, Fmet-leu-phe, interleukin-8, chemokine, cholecystokinin, endothelin, melanocortin, neuropeptide Y, neurotensin, opioid, somatostatin, tachykinin, thrombin vasopressin-like, galanin, proteinase activated, orexin and neuropeptide FF, adrenomedullin (G10D), GPR37/endothelin B-like, chemokine receptor-like and neuromedin U; hormone protein, rhodopsin, olfactory, prostanoid, nucleotide-like (adenosine, purinoceptors), cannabinoid, platelet activating factor, gonadotropin-releasing hormone, thyrotropin-releasing hormone and secretagogue, melatonin, lysosphingolipid, and LPA; Class B secretin-like g protein coupled receptors including, but not limited to, those which bind calcitonin, corticotropin releasing factor, gastric inhibitory peptide, glucagon, growth hormone-releasing hormone, parathyroid hormone, PACAP, secretin, vasoactive intestinal polypeptide, diuretic hormone, EMR1 and latrophilinl; class C metabotropic glutamate receptors including, but not limited to, those which bind metabotropic glutamate, extracellular calcium-sensing or GABA-B; receptor kinases; ion channels including, ionophores such as gramicidin, almaethicin, valinomycin, amphotericin B, and colcins; ligand gated channels such as acetylcholine receptor, glycine and GABA receptor, cytochrome oxidase, seratonin receptor, and IgE receptors; voltage gated channels such as, Na+ ion channel, K+ ion channel, chloride channel, and Ca2+ ion channel; light gated channels such as rhodopsin, and channelopsinl; active transport systems including, but not limited to, bacteriorhodopsin, $Ca^{2+}$-ATPase, $Na^+/K^+$ ATPase, $Na^+$-Glucose cotransport (Secondary), and $H^+/K^+$ ATPase ABC Transporters; porins, including alpha-hemolysin; and toxins such as diptheria and cholera toxins.

In some embodiments, the incorporated functioning protein may be bacteriorhodopsin. Bacteriorhodopsin (bR) is a 26 kDa transmembrane protein that uses a photochemical process to transport protons across the cell membrane against an electrochemical potential of up to 250 mV, translating to a 105 fold difference in proton concentration across the membrane. It is considered to be a prototype for a class of membrane transporters and also serves as a structural model for the G-protein-coupled receptors. (J.-P. Cartailler and H. Luecke, Annu. Rev. Biophys. Biomol. Struct. 326, 1317 (2003))

In another embodiment, the incorporated functioning protein may be gramicidin. Gramicidin is a model ion channel with alternating D and L amino acids. Gramicidin dimerizes to from a conductive state where two 15-amino acid peptides forming β-helices meet head to head at their N-termini in the interior of a lipid bilayer. The outer surface of the gramicidin that interacts with the lipids is hydrophobic in nature, and only monovalent cations pass through the more polar core of the helix. (A. Finkelstein and O. S. Andersen, J. Membr. Biol. 59, 155 (1981))

The hydrated polymer-lipid or polymer-lipid-biomolecular complex solution may additionally be coated onto a solid support. Coating may occur using any method known to those with skill in the art. In some embodiments, the solution is spin coated. In other embodiments, the solution is dip coated. In further embodiments, the solution may be deposited on a solid support using a combination of spin and dip coating. Solid supports may be macro or mesoporous. Exemplary solid supports include, but are not limited to, silicon wafer, silane-silicon, self assembled monolayer-gold, $SnO_2$, polymer coated substrates, gold, gold-SAM, or porous Alumina. Furthermore, solid supports may be planar or non-planar and formed as wafers or chips with regular or irregular surfaces, beads, microstructures, etc.

After coating, preferential evaporation of the solvent results in a concentration of lipids in a manner that allows their self-assembly into micellar and lyotropic liquid crystalline phases while a polymer matrix forms based on the organization of the lipid structures.

The formation of uniform nanostructures in the hybrid membranes of the present invention may be determined by any means applicable. In some embodiments, such determinations may be made using x-ray diffraction technology. Uniform nanostructures will generate regular d-spacings. In another embodiment, transmission electron microscopy may be used to determine the structure of the membranes. In a further embodiment, the orientation of functioning proteins may be examined by polarized Fourier transform infrared spectroscopy or secondary ion mass spectrometry.

The functioning of the incorporated proteins may be determined by any means applicable. For example, changes in hydrogen ion flux such as with the incorporation of gramicidin may be determined by impedance analysis. Ion sensitive fluorescent dies may be used to track gradients in ionic concentration. Electrophoretic mobility of ions through the hybrid membranes may also be characterized. Theoretical models of membrane transport may be used to calculate diffusion constants of ions, thus allowing quantitative comparisons between different membrane formulations. Additionally, membrane permeability in complex aqueous environments may also be determined. In a further embodiment, light induced pH changes caused by the proton pumping action of light activated proteins such as bacteriorhodobsin may be measured using pH meters and pH sensitive fluorescent dyes such as SNAFL-2 or fluorescein.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The following examples illustrate certain embodiments of the present invention, and are not to be construed as limiting the present disclosure. The evidence provided in these examples demonstrates methods based on sol-gel processing from the formation of robust thin films that incorporate phospholipid bilayer membranes and transmembrane proteins as multilamellar assemblies in cross-linked silica matrices.

Example I

Creation of Stock Sol Solution

Tetraethyl orthosilicate (TEOS), ethanol, deionized water, and 0.07 N HCl were mixed in the molar ratio of 1.0 TEOS: 3.8 $C_2H_5OH$: 1.0 $H_2O$: $5 \times 10^{-5}$ HCL and refluxed at 60° C. for 90 minutes. The resulting solution was diluted with 4 ml ethanol (1:2) followed by the addition of approximately 0.16 ml water and dilute 0.07 N HCl.

Example II

Lipid-Silica Thin Films

Various saturated and unsaturated lipids were used to prepare hybrid phospholipid-silica thin film assemblies by spin coating a mixture of lipids and a silica sol on silicon wafers. The following lipids, obtained from Avanti Polar Lipids (Alabaster, Ala.), 1,2-dimyristoyl-sn-glycero-3-phosphocholine (DMPC; 14:0); 1,2-dimyristoyl-sn-glycero-3-phosphoethanolamine (DMPE; 14:0); 1,2-dimyristoyl-sn-glycero-3-[phospho-rac-(1-glycerol)] (Sodium Salt) (DMPG, 14:0); 1-myristoyl-2-hydroxy-sn-glycero-3-phosphocholine (14:0 Lyso PC); 1,2-dioleoyl-sn-glycero-3-phosphocholine (DOPC; 18:1 (cis)); 1-oleoyl-2-hydroxy-sn-glycero-3-phosphoethanolamine (18:1 Lyso PE); 1,2-dioleoyl-sn-glycero-3-phosphoethanolamine (DOPE, 18:1); L-α-phosphatidylcholine (Egg) and 1,1',2,2'-tetramyristoyl cardiolipin (Ammonium Salt) (14:0), were prepared by evaporating the chloroform under a stream of nitrogen followed by desiccation under vacuum for at least 12 hrs.

Between 0.01 wt % to 10 wt % (typically from 0.1 mg to 100 mg of lipid) of dry phospholipids were added to the samples of the stock sol of Example I and hydrated for 1 hour. Each hydrated lipid solution was then homogenized by vortexing for 5 minutes at room temperature. The resulting solutions were then subjected to sonication for 5 minutes at room temperature using a VWR bath sonicator (power rating-9) (VWR International, West Chester, Pa.) before being coated at a speed of 3000 RPM for one minute onto silicon wafers which had previously been cleaned with a piranha solution of a 3:1 mixture of sulfuric acid and 30% hydrogen peroxide.

The resulting films were characterized using X-ray diffraction and transmission electron microscopy. X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques. As can be seen in FIG. 1A, which is representative of more than 25 samples, the d spacing observed for the film created using DMPC is 42 to 44 Å. Four order of diffraction peaks are observed for saturated lipids and the peak ratio is 1:2:3:4 exhibiting lamellar structure. Additionally, the x-ray diffraction pattern is most consistent with a lamellar phase structure with alternating phospholipid and silica layers that are parallel to the film surface. Further confirmation of a lamellar phase structure was determined by aging samples for 2 weeks for the condensation to take place. The samples were then subjected to calcination for four hours at 400° C. (heating rate of 1° C. per minute). Analysis of films that had been subjected to calcination revealed no peaks in the x-ray diffraction pattern indicating the collapse of the structure. Such a collapse is indicative of a lamellar formation.

Example III

Lipid-Water-Ethanol Films 2.5 mg of DMPC was dissolved in 50 µl ethanol and 50 µl water (pH 2.2) for one hour. The resulting solution was then coated onto silicon wafers.

Figure 2:
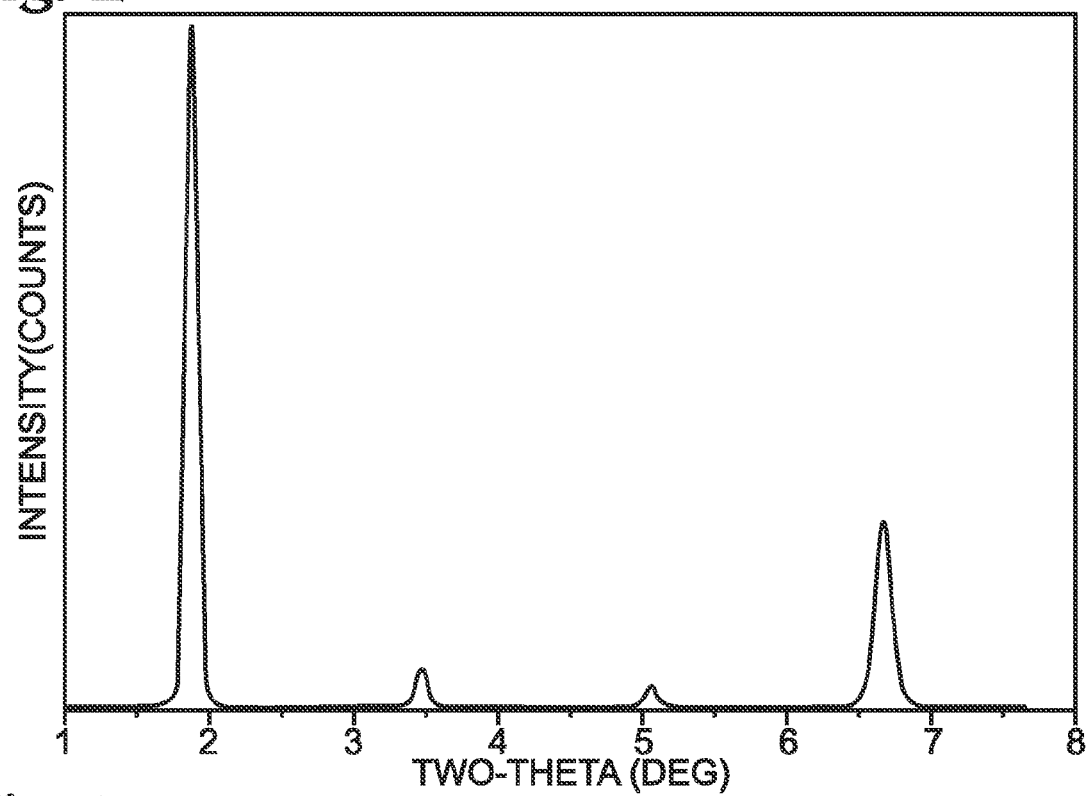
FIG. 2 is the x-ray diffraction pattern of 2.5% wt lipid-water-ethanol coated film on silicon wafer made using DMPC.

As can be seen in FIG. 2, the d-spacing obtained for the lipid-water system is 48 Å. The peaks are in a ratio of 1:2:3:4:5 demonstrating the lamellar structure of alternating lipid and water layers.

Preparations made with 2.5 mg of 1,2-dioleoyl-sn-glycero-3-phosphoethanolamine (DOPE) dissolved in 50 µl ethanol and 50 µl water (pH 2.2) for one hour and coated onto silicon wafers yielded inconsistent films with no definitive d spacing.

Example IV

Effect of Cholesterol on Lipid-Silica Assemblies

Egg phosphatidylcholine (Egg PC) is a mixture of phosphatidylcholines that differ in their fatty acid composition. The formulation used in this experiment was obtained from Avanti Polar Lipids (Alabaster, Ala.) and has a fatty acid distribution of 16:0 (34%), 16:1(2%), 18:0(11%), 18:1(32%), 18:2(18%), 20:4 (3%).

Lipid silica assemblies were prepared using Egg PC alone, cholesterol alone and varying mixtures of Egg PC and cholesterol. The Egg PC was prepared by hydrating Egg PC with stock sol of Example I for 1 hour. From 5 mol % to 50 mol % of cholesterol were added to aliquots of the hydrated Egg PC. The resulting mixtures were then individually homogenized by vortexing for 5 minutes at room temperature and then subjected to sonication for 5 minutes at room temperature using a VWR bath sonicator (power rating-9) (VWR International, West Chester, Pa.) before being coated at a speed of 3000 RPM for one minute onto silicon wafers which had previously been cleaned with a piranha solution of a 3:1 mixture of sulfuric acid and 30% hydrogen peroxide.

The resulting films were characterized using X-ray diffraction and transmission electron microscopy. X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques.

Figure 3:
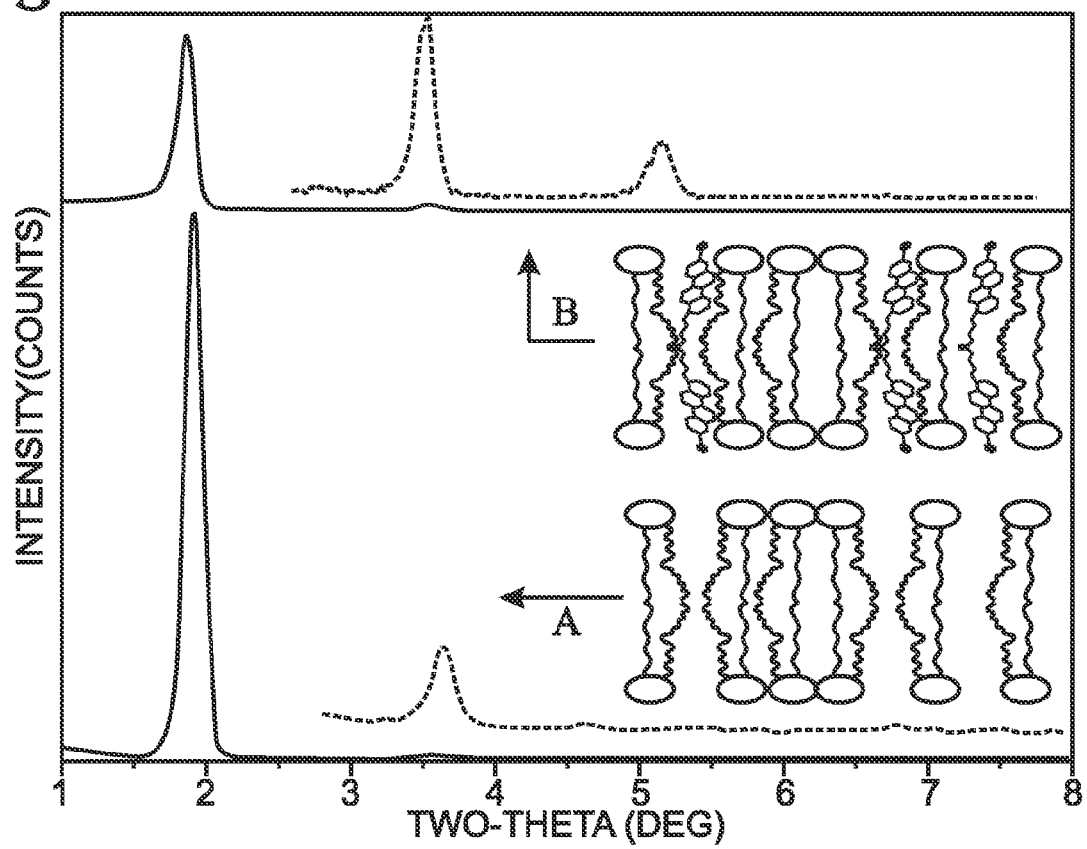
FIG. 3 shows the x-ray diffraction pattern of lipid EggPC-silica thin film (2.5 wt % lipid in stock sol) (A) before the addition of cholesterol and (B) after the addition of cholesterol (4:1 EggPC:cholesterol).

The x-ray diffraction pattern of a lipid-silica assembly made using the standard Egg PC can be seen in FIG. 3A. The x-ray diffraction pattern of a lipid-silica assembly made using Egg PC and cholesterol can be seen in FIG. 3B.

As seen in FIG. 3A, the lipid-silica assembly made using Egg PC alone had a d-spacing of 48-50 Å with only two peaks in the X-ray diffraction pattern. Transmission electron microscopy revealed the structure to be lamellar. The addition of cholesterol to the Egg PC-silica assembly increased the order of the x-ray diffraction pattern with new peaks at 31 Å and 16 Å suggesting the phase separation of the cholesterol-silica assembly (FIG. 3B). When cholesterol alone was used, peaks appeared at 31 Å and 16 Å, corresponding closely to a cholesterol bilayer that has a thickness of 33.9 Å.

Example V

Effect of Headgroup on Lipid-Silica Assemblies

Lipids with the same chain length but different head groups were used to prepare lipid-silica assemblies with a 2.5 wt % lipid composition. Lipid silica assemblies were prepared using DMPC, DMPE, DMPG, DMPS, DOPE, DOPA and DOPC respectively, all of which were obtained from Avanti Polar Lipids (Alabaster, Ala.). The lipids were prepared by hydrating each of them with stock sol of Example I for 1 hour. The resulting mixtures were then individually homogenized by vortexing for 5 minutes at room temperature and then subjected to sonication for 5 minutes at room temperature using a VWR bath sonicator (power rating-9) (VWR International, West Chester, Pa.) before being coated at a speed of 3000 RPM for one minute onto silicon wafers which had previously been cleaned with a piranha solution of a 3:1 mixture of sulfuric acid and 30% hydrogen peroxide.

The resulting films were characterized using X-ray diffraction and transmission electron microscopy. X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques.

Lipid-silica assemblies made with saturated lipids, DMPC, DMPE, and DMPS, all of which have a net positive charge on their head group at a pH of 2.2, yielded a d-spacing of 44 Å (FIG. 4A). DMPG, a saturated lipid with a neutral charge at pH 2.2 yielded a d-spacing of 47 Å DMPC and DMPE generated very long range order with $4^{th}$ order diffraction peaks in a ratio of 1:2:3:4. DMPG created two lamellar spacings. DMPS-silica assemblies do not create long-range order as observed in other saturated lipids. This is believed to be in part due to the carboxylic group in the headgroup of DMPS.

Lipid-silica assemblies made with unsaturated lipids DOPE and DOPC, both of which have a positive charge at pH 2.2, showed well defined lamellar structures with d-spacing corresponding to 48.4 Å and 47.4 Å with two orders of diffraction peaks as expected from unsaturated tails. No structure was obtained for lipid DOPA-silica assembly which has a negative charge at a pH 2.2.

The failure of the neutrally charged DMPG to generate long range order and of the negatively charged DOPA to form lipid-silica assemblies indicates the importance of the head group charge in the formation of assemblies.

Example VI

Effect of Combinations of Lipids on Lipid-Silica Assemblies

Lipid DOPE and EggPC in chloroform (Avanti Polar Lipids (Alabaster, Ala.)) were combined in a 1:1 ratio and hydrated for one hour with the stock sol of Example I. Aliquots of the resulting mixture were then homogenized by vortexing for 5 minutes at room temperature and then either coated directly onto silicon wafers or subjected to sonication for 5 minutes in an ice bath using a VWR bath sonicator (power rating-9) (VWR International, West Chester, Pa.) before being coated at a speed of 3000 RPM for one minute onto silicon wafers which had previously been cleaned with a piranha solution of a 3:1 mixture of sulfuric acid and 30% hydrogen peroxide.

The resulting films were characterized using X-ray diffraction and transmission electron microscopy. X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques.

Figure 5:
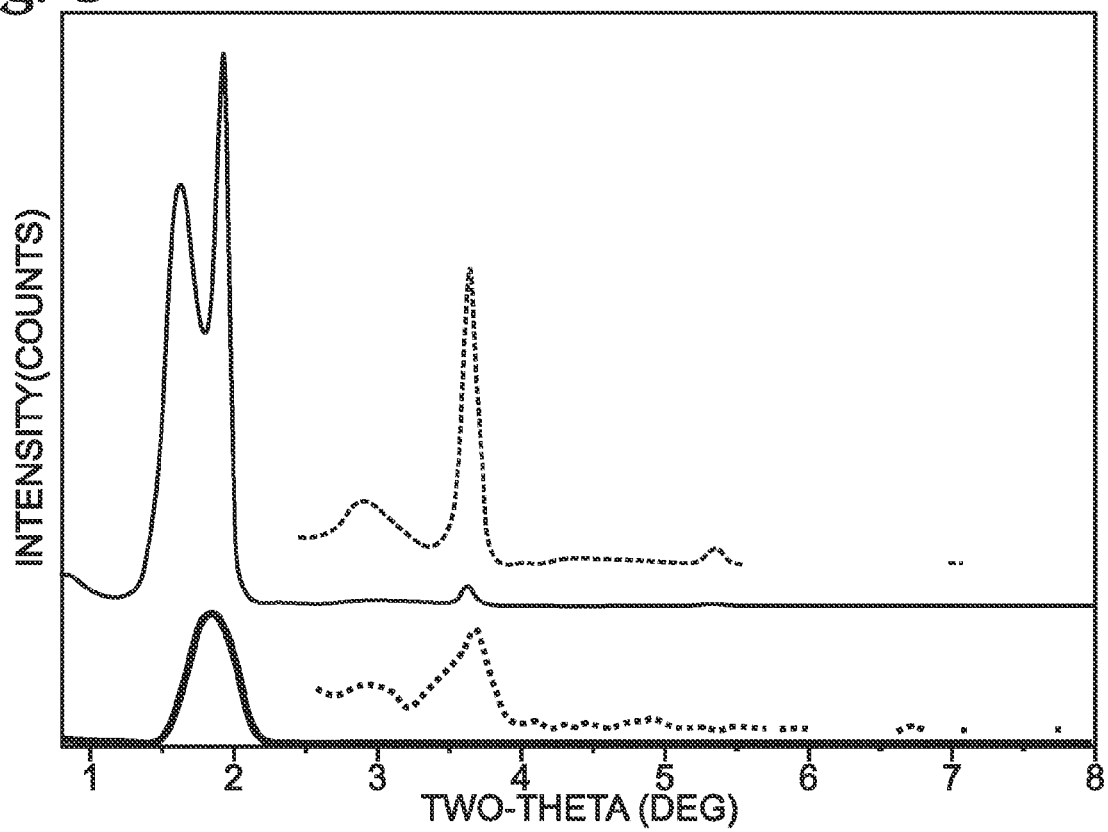
FIG. 5 shows the x-ray diffraction pattern of 2.5 wt % lipid-silica assemblies made using a 1:1 combination of EggPC and DOPE before sonication and after sonication.
Figure 6A:
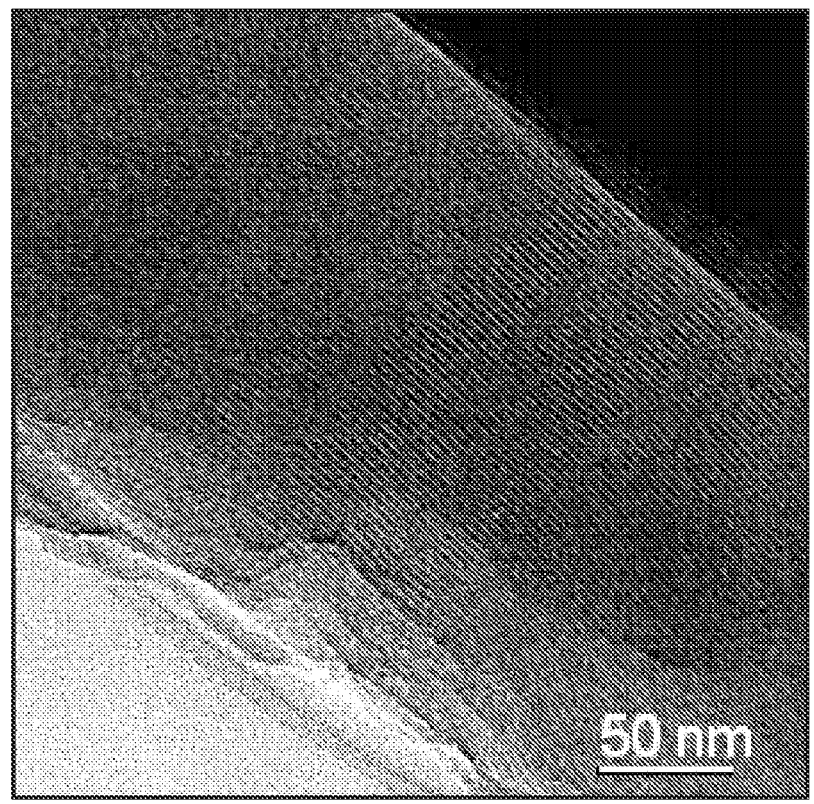
FIGS. 6A and B are micrographs of the surface of DOPE-silica thin films prepared with (A) 10 wt % DOPE in stock sol and (B) 1 wt % DOPE.
Figure 6B:
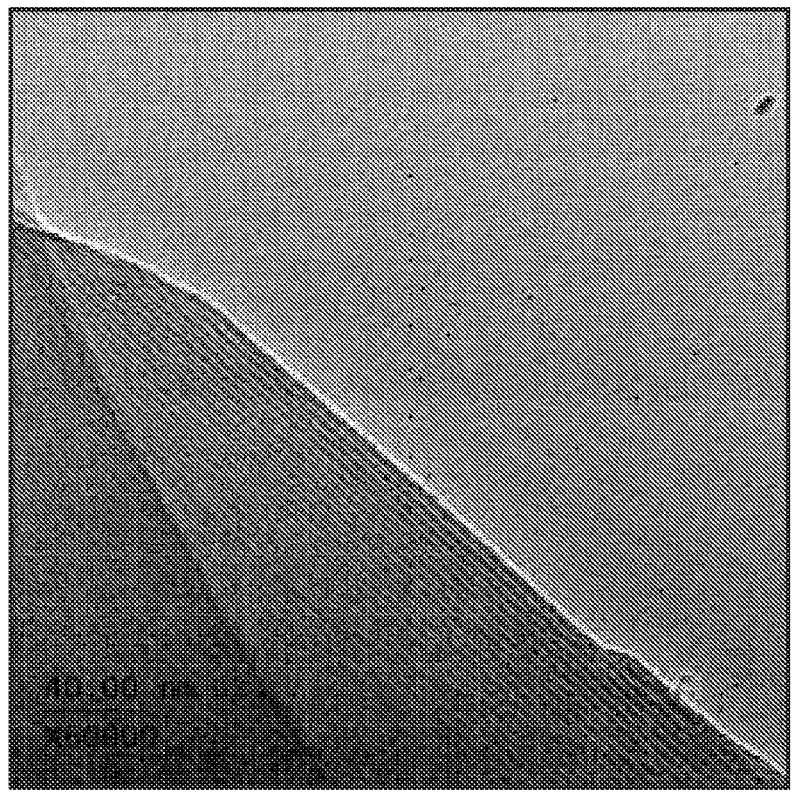
FIG. 6C is the X is the x-ray diffraction pattern of DOPE-silica films prepared from 10, 5.0, 2.5, 1 and 0.1 wt % DOPE.
Figure 6C:
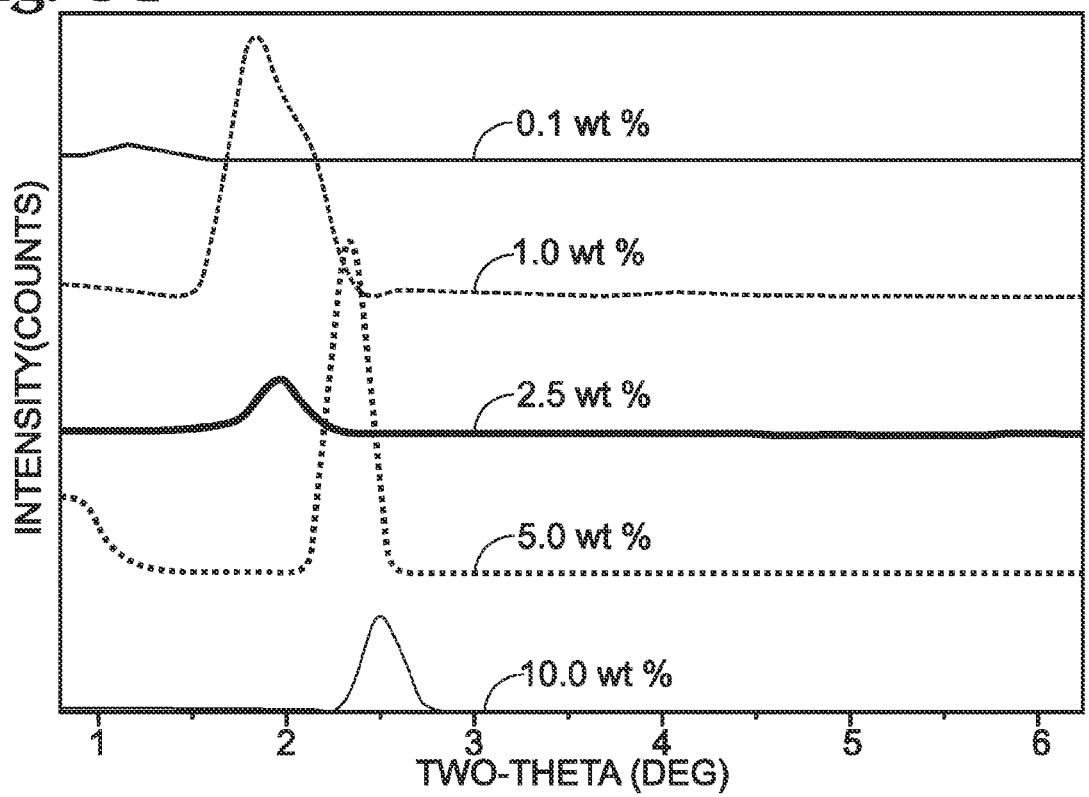

As can be seen in FIG. 5, two different lamellar assemblies were observed in the X-ray diffraction of the film made using the solution that was not subjected to sonication whereas only one lamellar assembly was visible in the X-ray diffraction of the film made using the solution that was subjected to sonication in an ice bath using a VWR bath sonicator (power rating-9) (West Chester, Pa.) for 1 hour with 1 minute rest every 15 minutes before being coated at a speed of 3000 RPM for one minute onto silicon wafers which had previously been cleaned with a piranha solution of a 3:1 mixture of sulfuric acid and 30% hydrogen peroxide.

Example VII

Vesicle Entrapment 1.25 mg of EggPC from Avanti Polar Lipids (Alabaster, Ala.) was dissolved in 200 µl of deionized water and hydrated for 1 hour. A portion of the resulting solution was treated to sonication at 4° C. using a VWR bath sonicator (power rating-9) (VWR International, West Chester, Pa.) for 1 hour with a one minute interval after every 15 minutes of sonication. 200 µl of stock sol from Example I was then added to this liposomal solution. The remainder of the solution was not treated to sonication. Both the sonicated and unsonicated solutions were coated at a speed of 3000 RPM for one minute onto silicon wafers which had previously been cleaned with a piranha solution of a 3:1 mixture of sulfuric acid and 30% hydrogen peroxide.

Figure 7A:
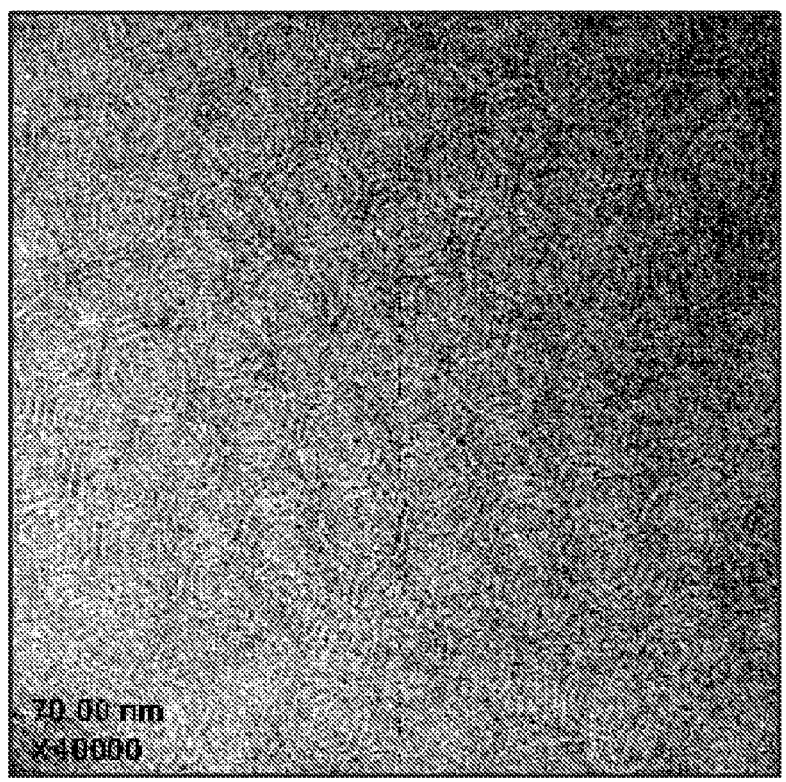
FIGS. 7A and B are images of the results of vesicle entrapment in lipid-silica assemblies made using EggPC taken using (A) TEM and (B) x-ray diffraction.
Figure 7B:
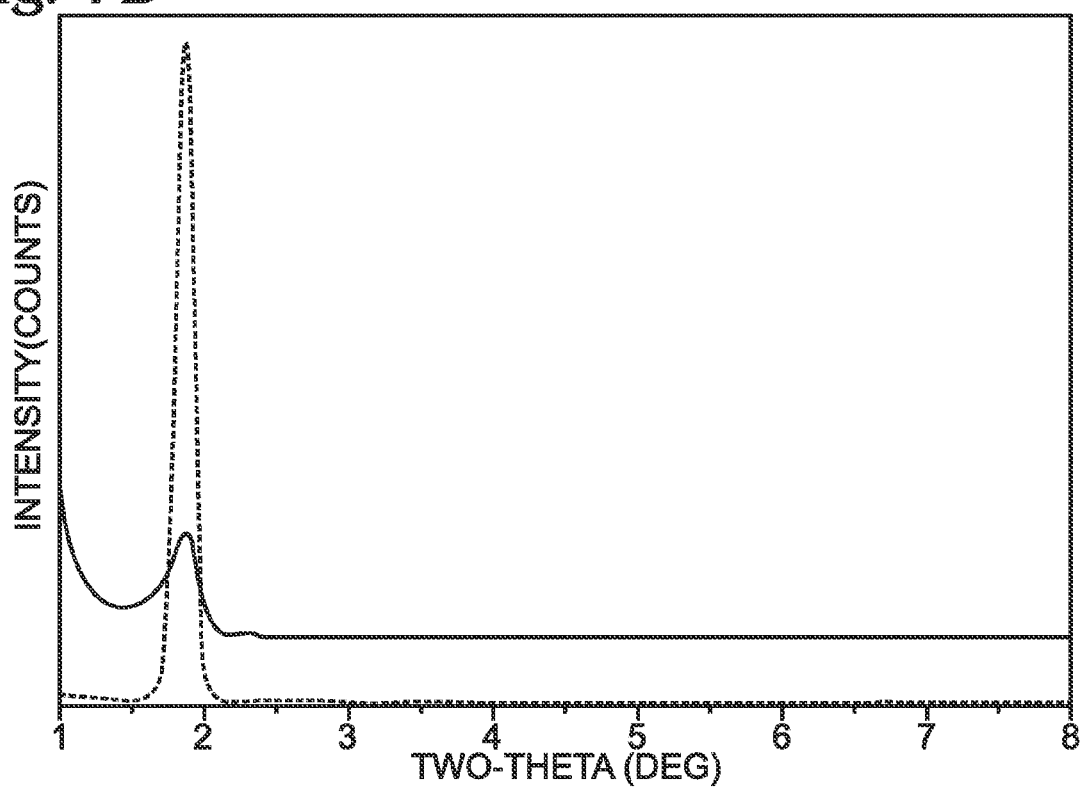

As can be seen in FIG. 7A, multilamellar vesicles of approximately 50 nm were packed together in a uniform manner in the film created using the sonicated sample. FIG. 7B provides a comparison of the x-ray diffraction pattern of the sonicated (upper line) and unsonicated samples (lower line).

Example VIII

Addition of Bacteriorhodopsin in Lipid-Silica Assemblies bR-containing purple membranes (lyophilized) composed primarily of phosphatidylglycerosulphate methyl ester and 3-HSO$_3$-Galp-β1, 6-Manp-α1,2-Glcp-α1,1-sn-2,3-diphytanylglycerol (Munich innovative Biomaterials GmbH, Germany) were combined with dried DOPE (Avanti Polar Lipids (Alabaster, Ala.)) at a ratio of 1:100. The resulting powder was then hydrated for one hour with stock sol from Example I. The resulting mixture was then homogenized by vortexing for 5 minutes at room temperature. The homogenized mixture was then either coated onto silicon wafers as it was, or subjected to sonication for 5 minutes at room temperature using a VWR bath sonicator (power rating-9) (VWR International, West Chester, Pa.) before being coated onto silicon wafers. Both solutions were coated at a speed of 3000 RPM for one minute onto silicon wafers which had previously been cleaned with a piranha solution of a 3:1 mixture of sulfuric acid and 30% hydrogen peroxide.

The resulting films were characterized using X-ray diffraction and transmission electron microscopy. X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques.

Figure 8A:
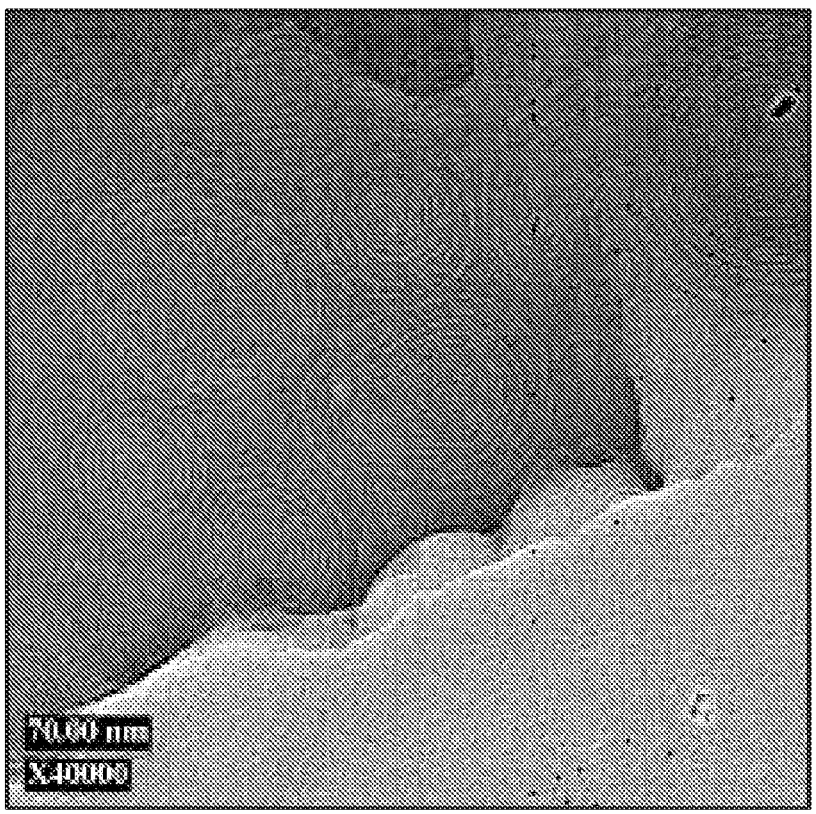
FIGS. 8A and B are TEM micrographs of DOPE-silica thin films prepared from 2.5 wt % DOPE and bacteriorhodopsin in a 100:1 DOPE:bR ratio (A) without sonication and (B) with sonication.

As can be seen in FIG. 8A, the TEM micrograph of a bR-DOPE-silica thin film without sonication shows the presence of multi-lamellar vesicle like structures. The x-ray diffraction pattern of the same film (FIG. 8C) shows two distinct peaks of different d-spacing with one peak corresponding to a d-spacing of ~46 Å and another peak corresponding to 53 Å. Analysis of a film prepared with a solution treated to sonication reveals planar lamellar structures (8B) and x-ray diffraction revealed a single d-spacing of ~46 Å.

Figure 8B:
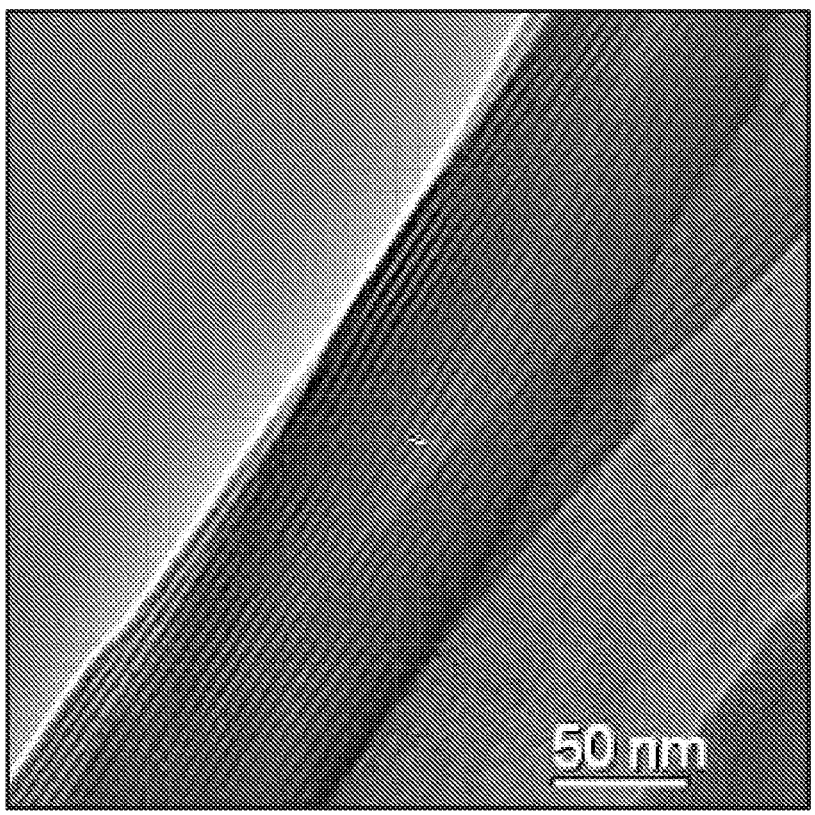
FIG. 8 C is an x-ray diffraction pattern of DOPE-silica thin films prepared from 2.5 wt % DOPE and bacteriorhodopsin in a 100:1 DOPE:bR ratio with and without sonication.
Figure 8C:
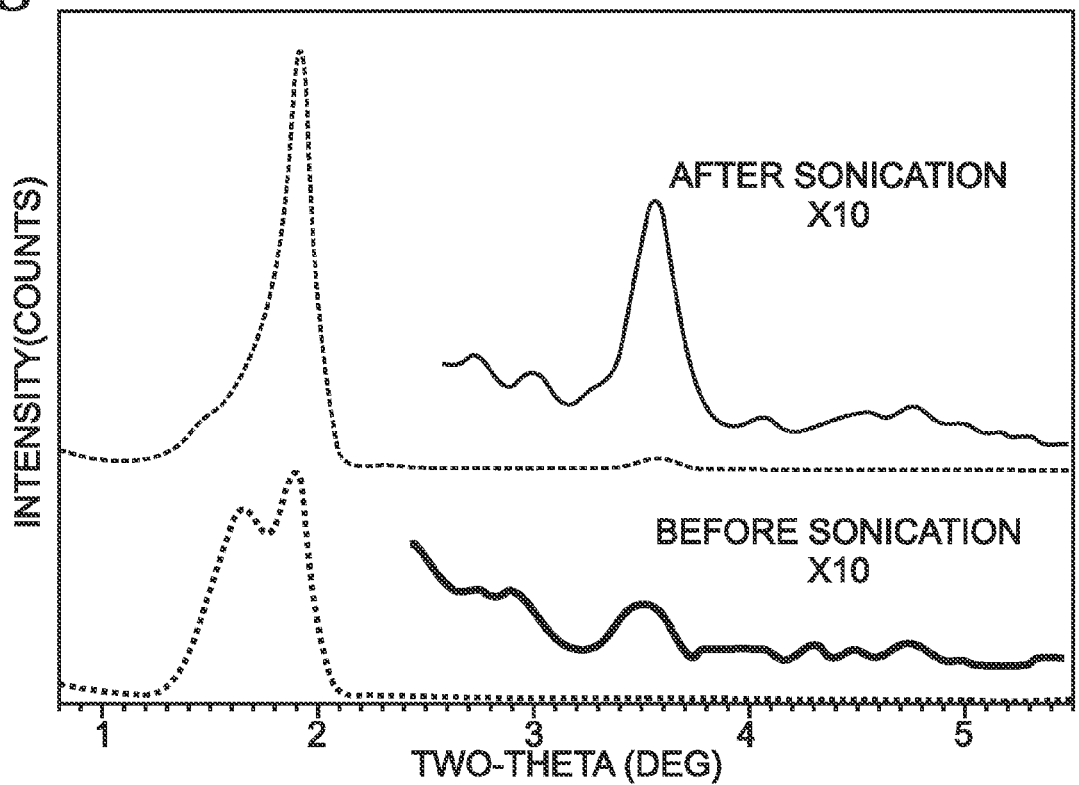
Figure 9A:
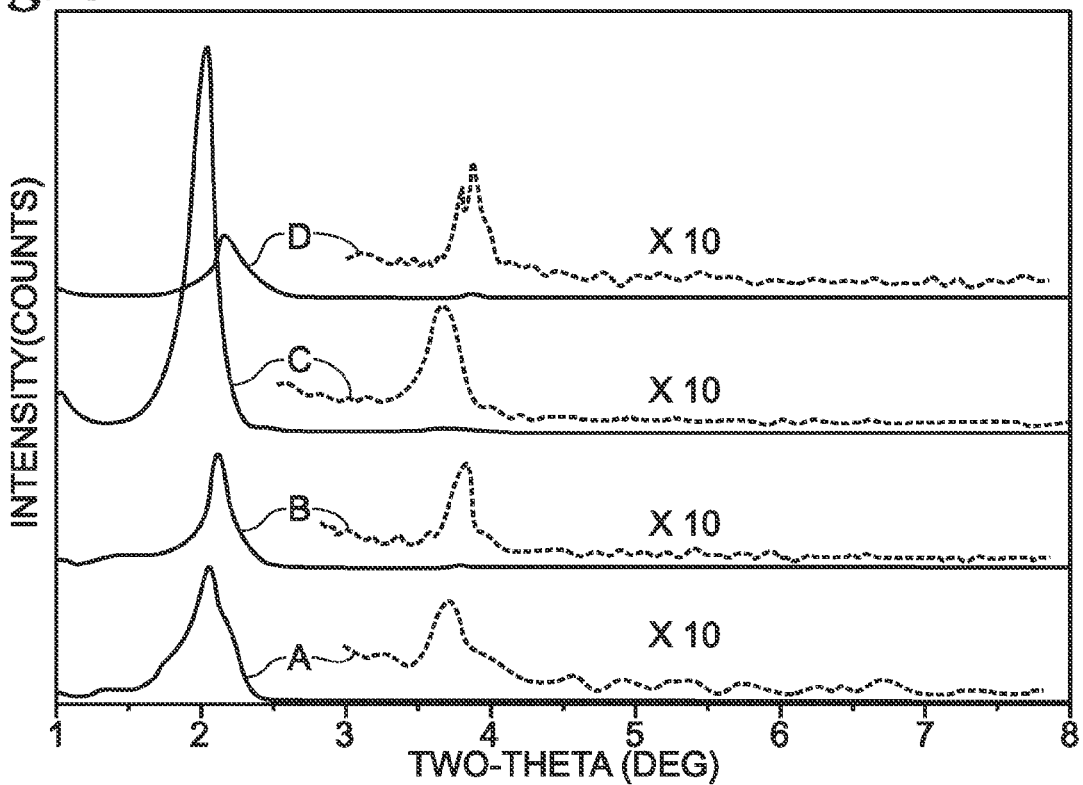
FIG. 9 shows the x-ray diffraction patterns of DOPE-silica thin films (A) with sonication, (B) without sonication, (C) with gramicidin but without sonication and (D) with gramicidin and sonication.
FIG. 9B is the transmission IR spectrum of gramicidin-DOPE-silica assemblies prepared with a 10:1 lipid:peptide ratio.
Figure 9B:
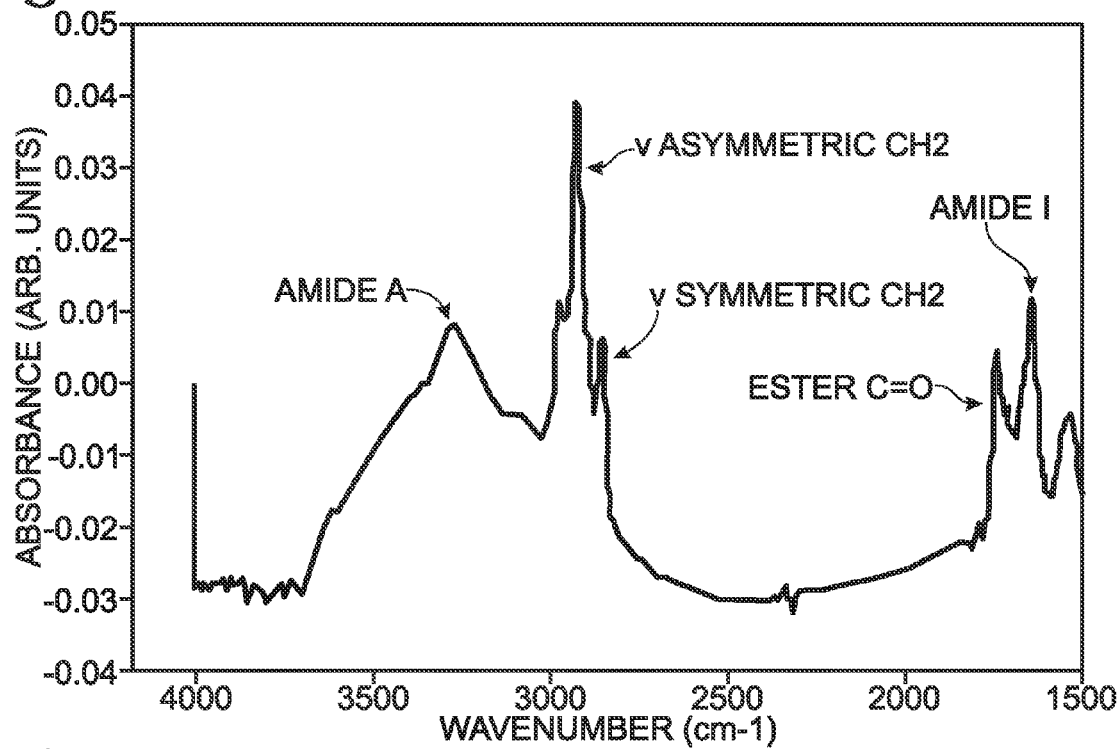

The purple membrane is composed primarily of phosphatidylglycerosulphate methyl ester and 3-HSO$_3$-Galp-β1, 6-Manp-α1,2-Glcp-α1,1-sn-2,3-diphytanylglycerol which generally creates a high negative charge density on the membrane surfaces and can therefore inhibit the formation of ordered lamellar structures. However, despite this limitation, as seen in FIG. 8, the inclusion of purple membrane components with the DOPE formulation results in the formation of multi-lamellar vesicle like structures.

Example IX

Incorporation of Gramicidin in DOPE-Silica Thin Films

Gramicidin (Sigma Aldrich (St. Louis, Mo.)) was combined with dried DOPE (Avanti Polar Lipids (Alabaster, Ala.)) at a ratio of 1:10. The resulting powder was then hydrated for one hour with stock sol from Example I. The resulting mixture was then homogenized by vortexing for 5 minutes at room temperature. The homogenized mixture was then either coated onto silicon wafers as it was, or subjected to sonication for 5 minutes at room temperature using a VWR bath sonicator (power rating-9) (VWR International, West Chester, Pa.) before being coated onto silicon wafers. Both solutions were coated at a speed of 3000 RPM for one minute onto silicon wafers which had previously been cleaned with a piranha solution of a 3:1 mixture of sulfuric acid and 30% hydrogen peroxide.

The resulting films were characterized using x-ray diffraction and transmission electron microscopy (TEM). X-ray diffraction was performed using a Siemens D500 diffractometer (NY, N.Y.) using Ni filtered CuKα radiation with λ-1.5406 Å in θ-2θ (2θ=0.8°–8.0°) step-scan mode using a step size 0.02° for 3 seconds. Transmission electron microscopy was performed using a JEOL 2010 (Tokyo, Japan) with 200 kv accelerating voltage equipped with a Gatan slow scan CCD camera (Pleasanton, Calif.). The samples were prepared either by scratching the films from silicon substrates using a cutting blade or by using standard cross-section techniques.

As can be seen in FIGS. 9A-D, the x-ray diffraction pattern of the DOPE-silica thin films with and without gramicidin are similar. This similarity was further confirmed by TEM analysis which revealed the planar lamellar structure of these films.

Although the foregoing invention has been described in detail by way of example for purposes of clarity of understanding, it will be apparent to the artisan that certain changes and modifications may be practiced within the scope of the appended claims which are presented by way of illustration not limitation. In this context it will be understood that this invention is not limited to the particular formulations, process steps, and materials disclosed herein as such formulations, process steps, and materials may vary somewhat. It will also be understood that the terminology employed herein is used for the purpose of describing particular embodiments only, and is not intended to be limiting since the scope of the present invention will be limited only by the appended claims and equivalents thereof. It is further noted that various publications and other reference information have been cited within the foregoing disclosure for economy of description. Each of these references are incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

REFERENCES

Alouf, J. E. 2001. "Pore-forming bacterial protein toxins: an overview". *Pore-Forming Toxins* 257:1-14.

Alves, I. D.; Salgado, G. F. J.; Salamon, Z.; Brown, M. F.; Tollin, G.; and Hruby, V. J.; *Biophysical Journal* 2005, 88, 198.

Asoh, H., K. Nishio, M. Nakao, A. Yokoo, T. Tamamura, and H. Masuda. 2001. "Fabrication of Ideally Ordered Anodic Porous Alumina with 63 nm Hole Periodicity Using Sulfuric Acid". *J Vac Sci Technol B* 19:569-572.

Baca, H. K.; Ph.D. Thesis, University of New Mexico, Albuquerque, N.Mex., 2005.

Bayley, H., O. Braha, and L. Q. Gu. 2000. "Stochastic sensing with protein pores". *Advanced Materials* 12: 139-142.

Bayley, H.; Braha, O.; Gu, L Q. *Advanced Materials.* 2000, 12, 139.

Blank, M. 1995. "Electric and Magnetic-Field Signal-Transduction in the Membrane Na+/K+-Adenosine-Triphosphatase". *Advances Chem* 250:339-248.

Bore, M. T.; Rathod, S. B.; Ward, T. L.; Datye, A. K.; *Langmuir* 2003, 19, 256. [38]

Knight, C. G.; *Liposomes from physical structure to therapeutic applications.* ElseiverlNorth-Holland Biomedical Press. 1981, Ch. 8.

Brinker, C. J., and G. W. Scherrer. 1900. *Sol-Gel Science.* Academic Press.

Brinker, C. J., Y. Lu, A. Sellinger, and H. Fan. 1999. "Evaporation-Induced Self-Assembly: Nanostructures Made Easy". *Adv. Mater.* 11:579-585.

Buranda, T., J. Huang, G. V. Rama Rao, L. K. Ista, R. S. Larson, T. L. Ward, L. A. Sklar, and G. P. Lopez. 2002. "Biomimetic Molecular Assemblies on Glass and Mesoporous Silica Microbeads for Biotechnological Applications". *Langmuir* In press.

Cartailler, J-P; Luecke, H.; *Annu. Rev. Biophys. Biomol. Struct.* 2003, 326, 1317. [18]

Lanyi, J. K.; Pohorille, A.; *Trends Biotechnol* 2001, 19, 140.

Caruso, R. A.; Antonietti, M.; *Chemistry of Materials.* 2001, 13, 3272.

Chilkoti, A., G. H. Chen, P. S. Stayton, and A. S. Hoffman. 1994. "Site-Specific Conjugation of a Temperature-Sensitive Polymer to a Genetically-Engineered Protein" *Bioconjugate Chem* 5:504-507.

Coleman, N. R. B.; Attard, G. S.; *Microporous and Mesoporous Materials.* 2001, 44, 73

Cornell, B. A., V. L. B. Braach-Maksvytis, L. G. King, P. D. J. Osman, B. Raguse, L. Wieczorek, and R. J. Pace. 1991. "A Biosensor that Uses Ion-Channel Switches". *Nature* 387: 580-583.

Doshi, D. A., N. K. Huesing, H. Y. Fan, K. S. Potter, B. G. Potter, A. J. Hurd, and C. J. Brinker. 2000. "Optically, Defined Multifunctional Patterning of Photosensitive Thin-Film Silica Mesophases". *Science* 290: 107-111.

Du, P., and I. Alkorta. 1994. "Sequence Divergence Analysis for the Prediction of 7-Helix Membrane-Protein Structures. 1. Comparison with Bacteriorhodopsin". *Protein Eng* 7:1221-1229.

Edman, K., P. Nollert, A. Royant, H. Belrhali, E. Pebay-Peyroula, J. Hajdu, R. Neutze, and E. M. Landau. 1999. "High-Resolution X-Ray Structure of an Early Intermediate in the Bacteriorhodopsin Photocycle". *Nature* 401:822-826.

Fernandez-Lopez, S., H. S. Kim, E. C. Choi, M. Delgado, J. R. Granja, A. Khasanov, K. Kraehenbuehl, G. Long, D. A. Weingberger, K. M. Wilcoxen, and M. R. Ghadiri. 2001. "Antibacterial agents based on the cyclic D,L-alpha-peptide architecture". *Nature* 414:329-329.

Garavito, R. M.; Ferguson-Miller, S.; *J. Biol. Chem.* 2001, 276, 32403

Garza, A. G., H. L. W., R. A. Stoebner, and M. D. Manson. 1995. "Motility Protein Interactions in the Bacterial Flagellar Motor". *Proc Natl Acad Sci USA* 92:1970-1974.

Harris, R. A., and A. M. Allan. 1985. "Functional Coupling of Gamma-Aminobutyric Acid Receptors to Chloride Channels in Brain Membranes". *Science* 228:1108-1110.

Haupts, U., J. Tittor, and D. Oesterhelt. 1999. "Closing in on Bacteriorhodopsin: Progress in Understanding the Molecule". *Annu Rev Biophys Biomed Struct* 28:367-399.

He, J. A., L. Samuelson, L. Li, J. Kumar, and S. K. Tripathy. 1999. "Bacteriorhodopsin Thin Film Assemblies: Immobilization, Properties, and Applications". *Adv Mater* 11:435-446.

He, J. A.; Samuelson, L.; Li, L.; Kumar, J.; Tripathy, S. K.; *Advanced Materials* 1999, 11, 435.

Hoffman, A. S., P. S. Stayton, T. Shimoboji, G. H. Chen, Z. L. Ding, A. Chilkoti, C. Long, M. Miura, J. P. Chen, T. Park, N. Monji, C. A. Cole, J. M. Harris, and K. Nakamae. 1997. "Conjugates of Stimuli-Responsive Polymers and Biomolecules: Random and Site-Specific Conjugates of Temperature-Sensitive Polymers and Proteins". *Macromolec Symp* 118:553-563.

Hoffman, A. S., P. S. Stayton, V. Bulmus, G. H. Chen, J. P. Chen, C. Cheung, A. Chilkoti, Z. L. Ding, L. C. Dong, R. Fong, C. A. Lackey, C. J. Long, M. Miura, J. E. Morris, N. Murthy, Y. Nabeshima, T. G. Park, O. W. Press, T. Shimoboji, S. Shoemaker, H. J. Yang, N. Monji, R. C. Nowinski, C. A. Cole, J. H. Priest, J. M. Harris, K. Nakamae, T. Nishinom, and T. Miyata. 2000. "Really Smart Bioconjugates of Smart Polymers and Receptor Proteins". *J Biomed Mater Res* 52:140-144.

Ishibashi, K., M. Kuwahara, and S. Sasaki. 2000. "Molecular Biology of Aquaporins". *Rev Physiol Bioch P* 14:1-32.

Ishibashi, K.; Kuwahara, M.; Sasaki, S.; *Rev. Physiol Bioch P* 2000, 14, 1.

Ista, L. K., S. Mendez, V. H. Perez-Luna, and Lopez G P. 2001. "Synthesis of Poly(NIsopropylacrylamide) on Initiator-Modified Self-Assembled Monolayers". *Langmuir* 17:2552-2555.

Ista, L. K., V. H. Perez-Luna, and G. P. Lopez. 1999. "Surface-Grafted, Environmentally Sensitive Polymers for Biofilm Release". *Appl. Environ. Microbiol.* 65:1603-1609.

J. N. Israelachivili, J. N.; *Intermolecular & Surface forces* by Second Edition. 1992. [28]

Karkamkar, A. J.; Kim, S. S.; Mahanti, S. D.; Pinnavaia, T. J.; *Advanced Functional Materials,* 2004, 14, 507-512

Kleinschmidt, J. H.; Tamm, L. K.; *Biophysical Journal* 2002, 83 994-1003

Konig, J., A. T. Nies, Y. H. Cui, I. Leier, and D. Keppler. 1999. "Conjugate Export Pumps of the Multidrug Resistance Protein (MRP) Family: Localization, Substrate Specificity, and MRP2-Mediated Drug Resistance". *BBA Biomembranes* 1461:377-394.

Ko'ta, Z.; Pa'Li, T.; and Marsh D.; *Biophysical Journal* 2004, 86, 1521-1531

Kuramoto, N., and Y. Shishido. 1998. "Property of Thermo-Sensitive and Redox Active Poly(N-Cyclopropylacrylamide-co-vinylferrocene) and Poly(N-Isopropylacrylamidecovinylferrocene)". *Polymer* 39:669-673.

Lanyi, J. K., and A. Pohorille. 2001. "Proton Pumps: Mechanism of Action and Applications". *Trends Biotechnol* 19: 140-144.

Lu, Y.; Ganguli, R.; Drewien, C. A.; Anderson, M. T.; Brinker, C. J.; Gong, W.; Guo, Y.; Soyez, H.; Dunn, B.; Huang, M. H.; Zink, J. I.; *Nature*, 1997, 389, 364.

Lu, Y. F., Y. Yang, A. Sellinger, J. M. Lu, J. M. Huang, H. Y. Fan, R. Haddad, G. P. Lopez, A. R. Burns, D. Y. Sasaki, J. Shelnutt, and C. J. Brinker. 2001. "Self-Assembly of Mesoscopically Ordered Chromatic Polydiacetylene/ Silica Nanocomposites". *Nature* 411:913-917.

Lu, Y. F.; Yang, Y.; Sellinger, A.; Lu, J. M.; Huang, J. M.; Fan, H. Y.; Haddad, R.; Lopez, G. P.; Burns, A. R.; Sasaki, D. Y.; Shelnutt, J.; Brinker, C. J. *Nature* 2001, 411, 913.

Lu, Y. F., H. Y. Fan, N. Doke, D. A. Loy, R. A. Assink, D. A. LaVan, and C. J. Brinker. 2000. "Evaporation-Induced Self-Assembly of Hybrid Bridged Silsesquioxane Film and Particulate Mesophases with Integral Organic Functionality". *Journal of The American Chemical Society* 122: 5258-5261.

Luecke, H., B. Schobert, H. T. Richter, J. P. Cartailler, and J. K. Lanyi. 1999. "Structural Changes inn Bacteriorhodopsin During Ion Transport at 2 Angstrom Resolution". *Science* 286:255-260.

Luo, T. J. M.; Soong, R.; Lan, E.; Dunn, B.; and Montemagno, C.; *Nature Materials* 2005, 5, 220.

Marsh, D.; *CRC Handbook of Lipid Bilayers* 1990.

Martinez-Landeira, P.; Ruso, J. M.; Prieto, G.; Sarmiento; F.; *Journal of Chemica and Engineering Data.* 2002, 47, 1017-1021

McCaughey, B.; Hampsey, J. E.; Wang, D.; Lu; Y.; *Encyclopedia of Nanoscience and Nanotechnology,* 2004, 9, 529-559.

Meyer, D. E., K. Trabbic-Carlson, and A. Chilkoti. 2001. "Protein Purification by Fusion with an Environmentally Responsive Elastin-Like Polypeptide: Effect of Polypeptide Length on the Purification of Thioredoxin". *Bzotechnol Progr* 17:720-728.

Meyer, D., and A. Chilkoti. 1999. "Purification of Recombinant Proteins by Fusion with Thermally-Responsive Polypeptides". *Nut Biotechnol* 17:1112-1115.

Moeck, G. S., and J. W. Coulton. 1998. "TonB-Dependent Iron Acquisition: Mechanisms of Siderophore-Mediated Active Transport". *Mol Microbiol* 28:675-681.

Moeck, G. S.; and Coulton, J. W. *J. Mol. Microbial.* 1998, 28, 675.

Nakane, J., M. Akeson, and A. Marziali. 2002. "Evaluation of nanopores as candidates for electronic analyte detection". *Electrophoresis* 23:2592-2601.

Nath, N., and A. Chilkoti. 2001. "Interfacial Phase Transition of an Environmentally Responsive Elastin Biopolymer Adsorbed on Functionalized Gold Nanoparticles Studied by Colloidal Surface Plasmon Resonance". *J Arner Chem Soc* 123:8197-8202.

Nelson, D. L.; M. M. Cox, M. M. *Lehninger Principles of Biochemistry,* 4th Edition. W. H. Freeman and Company, 2004; Ch. 11.

Nicolini, C. *Biosensors and Bioelectronics.* 1995, 10, 105.

Nicolini, C., V. Erokhin, S. Paddeu, and M. Sartore. 1998. "Towards a Light Addressable Transducer Bacteriorhodopsin-Based". *Nanotechnology* 9:222-227.

Nicolini, C.; Erokhin, V.; Paddeu, S.; Sartore, M.; *Nanotechnology* 1998, 9, 223. [24]

Finkelstein, A.; Andersen, O. S.; *J Membr Biol.* 1981, 59, 155.

Ottenbacher, D.; Kindervater, R.; Gimmel, P.; Klee, B.; Jahnig, F.; Gopel, W. *Sensors and Actuators B-Chemical.* 1992, 6, 192.

Parsons, S. M. 2000. "Transport Mechanisms in Acetylcholine And Monoamine Storage". *FASEB J* 14:2423-2434.

Parsons, S. M.; *FASEB J.* 2000, 14, 2423.

Philippot R. J.; Schuber, F. *Liposomes as tools in basic research and industry.* CRC Press 1995, Ch. 5.

Rama Rao, G. V., and G. P. L6pez. 2000. "Encapsulation of Poly(N-Isopropyl Acrylamide) in Silica: A Stimuli-Responsive Porous Hybrid Material that Incorporates Molecular Nano-Valves". *Advanced Materials* 12:1692-1695.

Rama Rao, G. V., G. P. Lopez, J. Bravo, H. Pham, A. K. Datye, H. Xu, and T. L. Ward. 2002. "Monodisperse Mesoporous Silica Microspheres Formed by Evaporation-Induced Self-Assembly of Surfactant Templates in Aerosols". *Advanced Materials* 14:1301-1304.

Rama Rao, G. V., S. Balarnurugan, D. E. Meyer, A. Chilkoti, and G. P. Lopez. 2002. "Hybrid bio-inorganic smart membranes that incorporate protein-based molecular switches". *Langmuir* 18:1819-1824.

Rama Rao, G. V.; Lopez, G. P.; Bravo, J.; Pham, H.; Datye, A. K.; Xu, H.; Ward, T. L. *Advanced materials.* 2002, 14, 1301.

Royant, A., K. Edman, T. Ursby, E. Pebay-Peyroula, E. M. Landau, and R. Neutze. 2000. "Helix Deformation Is Coupled to Vectorial Proton Transport in the Photocycle of Bacteriorhodopsin". *Nature* 406:645-648.

Sabine, J. R.; *Cholesterol.* 1977 Chapter 2, 5-26.

Stayton, P. S., T. Shimoboji, C. Long, A. Chilkoti, G. H. Chen, J. M. Harris, and A. S. Hoffman. 1995. "Control of Protein-Ligand Recognition Using a Stimuli-Responsive Polymer". *Nature* 378:472-474.

Stoeckenius, W. 1999. "Bacterial Rhodopsins: Evolution of a Mechanistic Model for the Ion Pumps". *Protein Sci* 8:447-459.

Stryer, J; Biochemistry, 4th Edition, W. H. Freeman and Company, 1995, Ch. 12.

Su, L. Y.; Hawkridge, F. M.; Rohten, M. C. *Chemistry and Biodiversity.* 2004, 1, 1281.

Urry, D. W. 1997. "Physical Chemistry of Biological Free Energy Transduction as Demonstrated by Protein-Based Polymers". *J. Phys. Chem. B* 101:11007-11028.

Yamaguchi, S.; Hong, T.; Waring, A.; Lehrer, R. I.; Hong, M.; *Biochemistry* 2002, 4, 9852.

Yamanaka, S. A.; Charych, D. H.; Loy, D. A.; and Sasaki, D. Y.; *Langmuir* 1997, 13, 5049.

Yan, J. C., L. M. Tender, P. D. Hampton, and G. P. Lopez. 2001. "Direct Electrochemical Transduction of Biorecognition at Viologen-Containing Monolayer Surfaces". *J Phys Chem B* 105:8905-8910.

Yan, J. C., V. R. Goparaju, G. P. Lopez, and P. Atanasov. Unpublished data.

Yeagle, P.; *The Structure of Biological Membranes.* 1992. Chapter 1 to 4, 3-210

Cevc, G.; Watts, A.; Marsh, D.; *Biochemistry* 1981, 20, 4955-4965

Hayward, R. C., D. A. Saville, and I. A. Aksay. 2000. "Electrophoretic Assembly of Colloidal Crystals with Optically Tunable Micropatterns". *Nature* 404:56-59.

Delamarche, E., G. Sundarababu, H. Biebuyck, B. Michel, C. Gerber; H. Sigrist, H. Wolf, H. Ringsdorf, N. Xanthopoulos, and H. J. Mathieu. 1996. "Immobilization of Antibodies on a Photoactive Self-Assembled Monolayer on Gold". *Langmuir* 12:1997-2006.

Yen, H. R. H., J. D. Andrade, and J. Kopecek. "Optically Controlled Ligand Delivery 3. Photocleavage of 2-Nitrobenzyl Bonds at Solid Liquid Interfaces". *Polymer* 33:1783-1767 (1992).

We claim:

1. A method of preparing a lipid-polymer hybrid membrane comprising:
   (a) combining an organic polymer, solvent, acid and water to create a stock sol;
   (b) adding dried lipid to the stock sol;
   (c) allowing the lipid to hydrate in the stock sol to form a lipid-polymer sol mixture;
   (d) homogenizing the lipid-polymer sol mixture; and coating the resulting mixture onto a solid support to generate a lipid-polymer hybrid membrane on the support.

2. The method of claim 1, wherein the stock sol further comprises an inorganic polymer.

3. The method of claim 2, wherein the inorganic polymer is a silica.

4. The method of claim 2, wherein the organic or inorganic polymer is selected from the group consisting of polymers formed from tetramethylorthosilicate, tetraethylorthosilicate, aminopropyltrimethyoxysilane, hydroxymethyltriethoxysilane, methacryloxypropyl trimethoxysilane, or hydroxyethyl methacrylate.

5. The method of claim 1, wherein the solvent is ethanol.

6. The method of claim 1, wherein the acid is HCl.

7. The method of claim 1, wherein the lipid is 1,2-dimyristoyl-sn-glycero-3-phosphocholine, 1,2-dimyristoyl-sn-glycero-3-phosphoethanolamine, 1,2-dimyristoyl-sn-glycero-3-[phospho-rac-(1-glycerol)] (Sodium Salt), 1-myristoyl-2-hydroxy-sn-glycero-3-phosphocholine (14:0 Lyso PC), 1,2-dioleoyl-sn-glycero-3-phosphocholine, 1-oleoyl-2-hydroxy-sn-glycero-3-phosphoethanolamine, 1,2-dioleoyl-sn-glycero-3-phosphoethanolamine, L-α-phosphatidylcholine or 1,1',2,2'-tetramyristoyl cardiolipin.

8. The method of claim 1, wherein the solid support is silicon wafer, silane-silicon, self assembled monolayer-gold, $SnO_2$, polymer coated substrate, gold, or porous Alumina.

9. The method of claim 1, wherein the lipid comprises 10% by weight of the lipid-polymer sol mixture.

10. The method of claim 1, wherein the lipid comprises 1% by weight of the lipid-polymer sol mixture.

11. The method of claim 1, wherein the lipid-polymer sol mixtures is sonicated prior to coating.

12. The method of claim 1, wherein the lipid-polymer sol mixture of claim 1 further comprises cholesterol.

13. A method of preparing a lipid-polymer hybrid membrane incorporating functional proteins comprising:
   (a) combining an organic polymer, inorganic polymer, solvent, acid and water to create a stock sol;
   (b) combining lyophilized protein with dried lipid;
   (c) adding the stock sol to the combined protein and dried lipid;
   (d) allowing the lipid and protein to hydrate in the stock sol to form a protein-lipid-polymer sol mixture;
   (e) homogenizing the protein-lipid-polymer sol mixture; and
   (f) coating the resulting mixture onto a solid support to generate a protein-lipid-polymer hybrid membrane on the support.

14. The method of claim 13, wherein the protein is selected from the group consisting of a g couple protein receptor, an ion channel, a ligand gated channel, a voltage gated channel, a light gated channel, an active transport system, porins, alpha-hemolysin, or a toxin.

15. The method of claim 13, wherein the inorganic polymer is a silica.

16. The method of claim 13, wherein the lipid is selected from the group consisting of 1,2-dimyristoyl-sn-glycero-3-phosphocholine, 1,2-dimyristoyl-sn-glycero-3-phosphoethanolamine, 1,2-dimyristoyl-sn-glycero-3-[phospho-rac-(1-glycerol)] (Sodium Salt), 1-myristoyl-2-hydroxy-sn-glycero-3-phosphocholine (14:0 Lyso PC), 1,2-dioleoyl-sn-glycero-3-phosphocholine, 1-oleoyl-2-hydroxy-sn-glycero-3-phosphoethanolamine, 1,2-dioleoyl-sn-glycero-3-phosphoethanolamine, L-α-phosphatidylcholine or 1,1',2,2'-tetramyristoyl cardiolipin.

* * * * *